(12) United States Patent
Hayakawa et al.

(10) Patent No.: US 11,465,330 B2
(45) Date of Patent: Oct. 11, 2022

(54) METHOD AND APPARATUS FOR STERILIZING BOTTLE

(71) Applicant: Dai Nippon Printing Co., Ltd., Tokyo (JP)

(72) Inventors: Atsushi Hayakawa, Tokyo (JP); Yuiko Wada, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 224 days.

(21) Appl. No.: 15/031,373

(22) PCT Filed: Nov. 13, 2014

(86) PCT No.: PCT/JP2014/080052
§ 371 (c)(1),
(2) Date: Apr. 22, 2016

(87) PCT Pub. No.: WO2015/072506
PCT Pub. Date: May 21, 2015

(65) Prior Publication Data
US 2016/0257055 A1    Sep. 8, 2016

(30) Foreign Application Priority Data

Nov. 14, 2013  (JP) .............................. JP2013-235717
Oct. 17, 2014  (JP) .............................. JP2014-212982

(51) Int. Cl.
*A61L 2/06* (2006.01)
*A61L 2/20* (2006.01)
(Continued)

(52) U.S. Cl.
CPC ............... *B29C 49/46* (2013.01); *A61L 2/04* (2013.01); *A61L 2/06* (2013.01); *A61L 2/208* (2013.01);
(Continued)

(58) Field of Classification Search
CPC .................................. B29C 49/46; A61L 2/208
(Continued)

(56) References Cited

U.S. PATENT DOCUMENTS 1,364,360 A * 1/1921 Emery .................. F04D 25/084
                                                        417/234
4,026,982 A * 5/1977 Dardaine ................ B29C 49/18
                                                        264/525
(Continued)

FOREIGN PATENT DOCUMENTS

JP    04-044902 A1    2/1992
JP    H07-033123 A    2/1995
(Continued)

OTHER PUBLICATIONS

Polyethylene terephthalate, Encyclopaedia Britannica, https://www.britannica.com/science/polyethylene-terephthalate, Published Jun. 1, 2018. (Year: 2018).*

(Continued)

*Primary Examiner* — Kelly M Gambetta
*Assistant Examiner* — Russell E Sparks
(74) *Attorney, Agent, or Firm* — Burr & Brown, PLLC

(57) ABSTRACT

A step of letting a preform made of resin adsorb a sterilizer, a step of sterilizing the preform by heating the preform having adsorbed the sterilizer to a temperature suitable for a blow-molding treatment to activate the sterilizer adsorbed by the preform and a step of shaping the preform into a bottle by blowing aseptic air into the preform in a mold are performed sequentially. According to the above-mentioned steps, the sterilizer does not enter a blow-molding machine.

6 Claims, 21 Drawing Sheets

(51) Int. Cl.
  *B29C 49/42* (2006.01)
  *B29C 49/06* (2006.01)
  *A61L 2/18* (2006.01)
  *B29C 49/46* (2006.01)
  *A61L 2/04* (2006.01)
  *B29C 49/48* (2006.01)
  *B29C 49/64* (2006.01)
  *B29K 67/00* (2006.01)
  *B29L 31/00* (2006.01)

(52) U.S. Cl.
  CPC .............. *A61L 2/18* (2013.01); *A61L 2/186* (2013.01); *A61L 2/20* (2013.01); *A61L 2202/11* (2013.01); *A61L 2202/122* (2013.01); *A61L 2202/15* (2013.01); *A61L 2202/18* (2013.01); *A61L 2202/23* (2013.01); *B29C 49/06* (2013.01); *B29C 49/4205* (2013.01); *B29C 49/6409* (2013.01); *B29C 49/6418* (2013.01); *B29C 2049/4679* (2013.01); *B29C 2049/4697* (2013.01); *B29C 2049/4892* (2013.01); *B29K 2067/003* (2013.01); *B29L 2031/7158* (2013.01)

(58) Field of Classification Search
  USPC ........................................... 264/535
  See application file for complete search history.

(56) References Cited

U.S. PATENT DOCUMENTS

| | | | | |
|---|---|---|---|---|
| 5,997,827 | A * | 12/1999 | Mezger | A61L 2/208 261/142 |
| 6,270,868 | B1 * | 8/2001 | Matsui | B29C 49/20 215/12.1 |
| 6,562,281 | B1 | 5/2003 | Marchau et al. | |
| 6,692,684 | B1 * | 2/2004 | Nantin | B65B 55/06 264/521 |
| 8,039,022 | B2 * | 10/2011 | Minamikawa | A01N 59/00 422/28 |
| 8,092,757 | B2 * | 1/2012 | Adriansens | A61L 2/208 264/252 |
| 2007/0269339 | A1 * | 11/2007 | Frost | A61L 2/18 422/292 |
| 2008/0152538 | A1 | 6/2008 | Quetel et al. | |
| 2010/0047120 | A1 | 2/2010 | Adriansens et al. | |
| 2010/0170867 | A1 | 7/2010 | Hayakawa | |
| 2011/0072759 | A1 * | 3/2011 | Mielnik | A61L 2/208 53/167 |
| 2013/0133297 | A1 | 5/2013 | Adriansens | |
| 2014/0144105 | A1 | 5/2014 | Hayakawa et al. | |
| 2014/0311095 | A1 | 10/2014 | Hayakawa et al. | |

FOREIGN PATENT DOCUMENTS

| | | | | |
|---|---|---|---|---|
| JP | 08-091491 | A1 | 4/1996 | |
| JP | 2851383 | B | 1/1999 | |
| JP | 2000-128131 | A | 5/2000 | |
| JP | 2000-326935 | A1 | 11/2000 | |
| JP | 2001-510104 | A1 | 7/2001 | |
| JP | 2008-183899 | A1 | 8/2008 | |
| JP | 2008-546605 | A1 | 12/2008 | |
| JP | 2009-018850 | A1 | 1/2009 | |
| JP | 2009-166900 | A1 | 7/2009 | |
| JP | 2011-178402 | A1 | 9/2011 | |
| JP | 2013-035561 | A1 | 2/2013 | |
| JP | 2013-035562 | A1 | 2/2013 | |
| JP | 2013-528133 | A1 | 7/2013 | |
| JP | 2013-224183 | A1 | 10/2013 | |
| TR | 200001162 | * | 9/2000 | ............... A61L 2/10 |
| WO | 2013/021882 | A1 | 2/2013 | |
| WO | WO-2013021882 | A1 * | 2/2013 | ........... B67C 7/0073 |
| WO | 2013/061956 | A1 | 5/2013 | |

OTHER PUBLICATIONS https://patents.google.com/patent/WO2013021882A1/en. (Year: 2013).*
Machine Translation of 200001162 (Year: 2000).*
European Search Report, European Application No. 14862669.0, dated May 16, 2017 (8 pages).
International Search Report and Written Opinion (Application No. PCT/JP2014/080052) dated Feb. 3, 2015.
Japanese Office Action (Application No. 2018-219238) dated Jul. 16, 2019 (with English translation).
Japanese Office Action (Application No. 2018-239212) dated Dec. 3, 2019 (with English translation).
Japanese Office Action (with English translation), Japanese Application No. 2018-239212, dated Feb. 5, 2020 (4 pages).

* cited by examiner

FIG.5
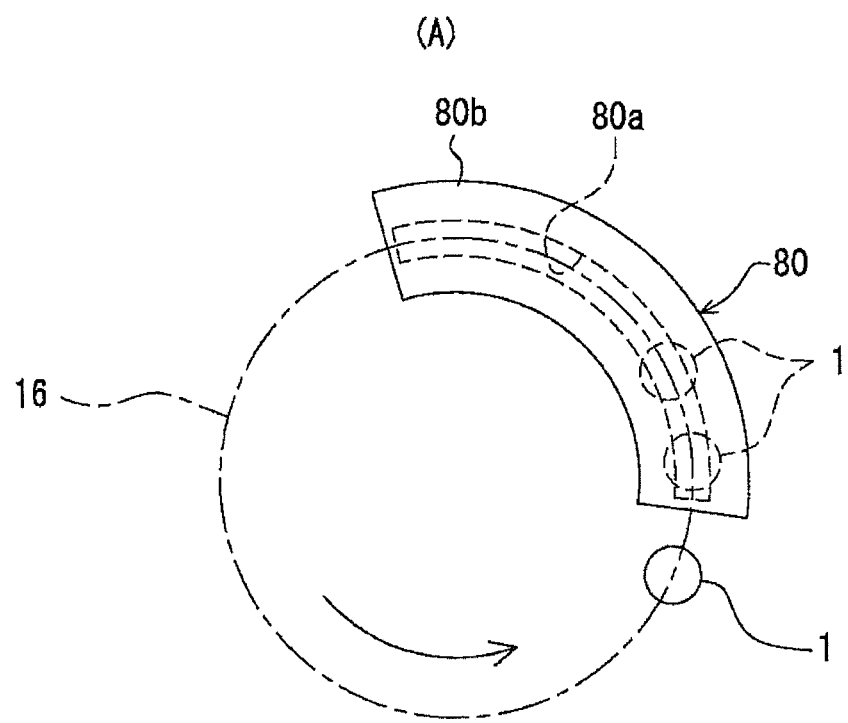
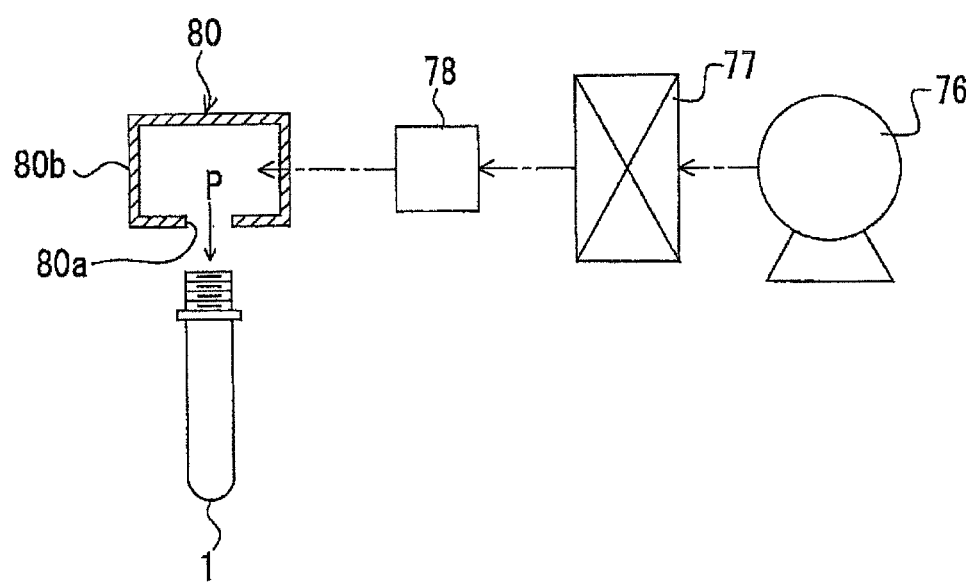

FIG.10
(A)
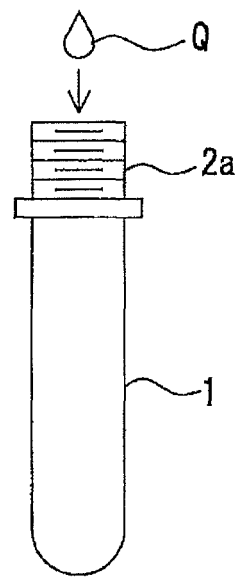
(B)
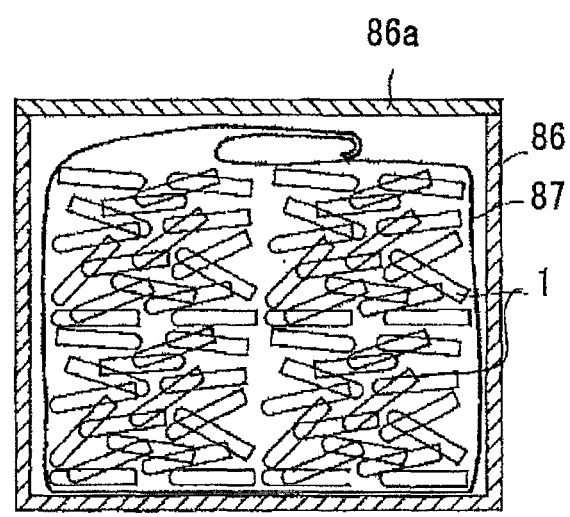

METHOD AND APPARATUS FOR STERILIZING BOTTLE

BACKGROUND OF THE INVENTION

1. Field of the Invention

The present invention relates to method and apparatus for sterilizing a bottle.

2. Description of Related Art

In conventional art, there is provided a bottle sterilizing method in which, while continuously conveying preforms, a sterilizer (sterilizing agent) is applied to the preforms, which are then introduced into a heating furnace, the preforms are heated in the heating furnace to a temperature suitable for forming the preform into a container, and the sterilizer applied to the preform is dried and activated simultaneously during such heating and the preform is then molded into a bottle. The bottle thus formed is in a sterilized state (see Patent Documents 1, 2, 3).

Furthermore, there is also provided a drink filling method in which a preform is preheated, hydrogen peroxide mist or gas is blasted to the preheated preform, the preform is then heated to a temperature suitable for molding thereof, the preform of the suitable temperature for molding is molded into a bottle in a mold continuously traveling with the preform, the blow-molded bottle is taken out of the mold, and thereafter, the bottle is filled up with drink and then sealed with a lid (for example, Patent Documents 4, 5).

Still furthermore, there is also provided a method in which a preform is dipped into a sterilizing liquid to thereby sterilize the preform, the preform is heated to a temperature suitable for molding in a heating furnace after the sterilizer liquid adheres to the preform has been removed, and the preform is thereafter blow-molded into a container (see Patent Document 6).

PRIOR ART DOCUMENT

Patent Document

Patent Document 1: Japanese Unexamined Patent Publication No. 2001-510104
Patent Document 2: Japanese Patent Laid-open Publication No. 2008-183899
Patent Document 3: Japanese Unexamined Patent Publication No. 2008-546605
Patent Document 4: Japanese Patent Laid-open Publication No. 2013-35561
Patent Document 5: Japanese Patent Laid-open Publication No. 2013-35562
Patent Document 6: Japanese Patent Laid-open Publication No. 4-44902

SUMMARY OF THE INVENTION

The conventional technologies described above concern to sterilization treatment of preforms before being molded to bottles. However, in such technologies, hydrogen peroxide adhering to the preform is introduced into a blow molding machine together with the preform, which may pose a fear such that the hydrogen peroxide introduced in the blow-molding machine will damage various members or components such as seal member within the blow-molding machine. In addition, in order to prevent the defective sterilization effect, if a lot of condensed mist of the hydrogen peroxide is blasted in the stage of the preform, the amount of the hydrogen peroxide adhering to the preforms may not become even, and as a result, uneven heating may be caused to the preforms before the blow-molding process, which may produce defective product of bottle such as bleaching, distortion and other defective in the molding process.

The present invention aims to solve such problems as mentioned above.

Means for Solving the Problems

In order to solve the above problems, the present invention adopts the following configuration or structure.

It is further to be noted that although the description is made with parentheses to reference numerals for easy understanding of the invention, the present invention is not limited thereto.

That is, the present invention according to a first aspect adopts a method of sterilizing a bottle, comprising the steps of: letting a preform (1) made of resin adsorb a sterilizer; sterilizing the preform (1) by heating the preform (1) having adsorbed the sterilizer to a temperature suitable for a blow-molding treatment to activate the sterilizer adsorbed by the preform (1); and shaping the preform (1) into a bottle (2) by blowing air into the preform (1) in a mold (4), wherein the above-mentioned steps are performed sequentially.

According to a second aspect of the present invention, it may be preferred that, in the bottle sterilizing method according to the first aspect, the preform (1) is allowed to adsorb the sterilizer by gasifying the sterilizer and discharging the sterilizer gas (G) toward the preform (1) from a nozzle (6).

According to a third aspect of the present invention, it may be preferred that, in the bottle sterilizing method according to the second aspect, the preform (1) is allowed to adsorb the sterilizer by atomizing the sterilizer in an evaporator (9) to gasify the sterilizer and discharging the gas toward the preform (1) from a nozzle (6) of the evaporator (9).

According to a fourth aspect of the present invention, it may be preferred that, in the bottle sterilizing method according to the second or third aspects, air (P) is blasted to the preform (1) with the sterilizer adhering thereto to remove an excess of the sterilizer from the preform (1) and let the preform (1) adsorb the sterilizer.

According to a fifth aspect of the present invention, it may be preferred that, in the bottle sterilizing method according to the first aspect, the preform (1) is allowed to absorb the sterilizer by dripping the sterilizer to the preform (1) and performing aging on the preform (1) in a sealed chamber.

According to a sixth aspect of the present invention, it may be preferred that, in the bottle sterilizing method according to any one of the first to fifth aspects, the sterilizer is a solution including at least 1% by mass of hydrogen peroxide component.

According to a seventh aspect of the present invention, it may be preferred that, in the bottle sterilizing method according to the first aspect, an umbrella-shaped member covers above the mouth portion of the preform at a time when the preform is heated to a temperature for a blow-molding step.

According to an eighth aspect of the present invention, it may be preferred that, in the bottle sterilizing method according to the first aspect, an aseptic air is blasted to the mouth portion of the preform at a time when the preform is conveyed toward the mold after heating the preform to the temperature for the blow-molding step.

The present invention according to a ninth aspect adopts an apparatus for sterilizing a bottle, comprising: a transfer unit that transfers a preform (1) having adsorbed a sterilizer or a bottle (2) from a supplying stage of the preform (1) to a molding stage of the bottle (2); a heating furnace (33) that heats the preform (1) to a temperature for a blow-molding treatment to activate the sterilizer adsorbed by the preform (1), thereby sterilizing the preform (1); and a mold (4) that blow-molds the preform (1) into the bottle (2) by air, wherein the heating furnace (33) and the mold (4) are arranged in series from an upstream side toward a downstream side of the transfer unit.

According to a tenth aspect of the present invention, it may be preferred that, in the bottle sterilizing apparatus according to the ninth aspect, an evaporator (9) that gasify the sterilizer atomized by a spray nozzle (8), a sterilizer supplying nozzle (6) that discharges the gas (G) produced by the evaporator (9) toward the preform (1), and an air nozzle (80) that blasts air (P) to the preform (1) with the sterilizer discharged from the sterilizer supplying nozzle (6) adhering thereto to remove an excess of the sterilizer from the preform (1) and let the preform (1) adsorb the sterilizer are arranged in the transfer unit.

According to an eleventh aspect of the present invention, it may be preferred that, in the bottle sterilizing apparatus according to the ninth or tenth aspects, the sterilizer is a solution including at least 1% by mass of hydrogen peroxide component.

According to a twelfth aspect of the present invention, it may be preferred that, in the bottle sterilizing apparatus according to the ninth aspect, an umbrella-shaped member that covers above the mouth portion of the preform is provided within the heating furnace.

According to a thirteenth aspect of the present invention, it may be preferred that, in the bottle sterilizing apparatus according to the ninth aspect, a cover is arranged on a way of a bottle traveling path along which the preform travels from the heating furnace to the mold for blow-molding, and an aseptic air is blasted from the cover side toward the mouth portion of the preform.

DETAILED DESCRIPTION OF THE INVENTION

In the bottle sterilizing method according to the present invention, a step of letting a preform (1) made of resin adsorb a sterilizer, a step of sterilizing the preform (1) by heating the preform (1) having adsorbed the sterilizer to a temperature suitable for a blow-molding treatment to activate the sterilizer adsorbed by the preform (1), and a step of shaping the preform (1) into a bottle (2) by blowing aseptic air into the preform (1) in a mold (4) are performed sequentially, and only the sterilizer, such as hydrogen peroxide adsorbed by the preform (1), is introduced into the blow-molding machine (12) along with the preform (1). Thus, the sterilizer can be prevented from entering the blow-molding machine (12) by itself, and various devices in the blow-molding machine (12) can be prevented from being damaged by the sterilizer.

In addition, since there is no sterilizer condensate adhering to the surface of the preform (1) conveyed into the blow-molding machine (12), molding defects, such as whitening, distortion or uneven molding, can be prevented from occurring when the bottle (2) is molded.

Since the sterilizer adsorbed by the preform (1) is heated along with the preform (1) to a temperature suitable for a blow-molding treatment and thereby activated, any bacteria on the preform (1) is adequately sterilized. Thus, the sterilization effect on the preform (1) is improved, and the sterilization effect on the bottle (2) is also improved.

BRIEF DESCRIPTION OF THE DRAWINGS

FIG. 5 shows an air nozzle to be incorporated in the bottle sterilizing apparatus according to the present invention, in which (A) is a plan view thereof and (B) is a vertical sectional view thereof.

FIG. 10 represents a bottle sterilizing method according to a second embodiment of the present invention, in which (A) shows a step of dripping a hydrogen peroxide solution into a preform, and (B) shows a step of performing aging on the preform in which the hydrogen peroxide solution has been dripped.

EMBODIMENT FOR CARRYING OUT THE INVENTION

Hereunder, embodiments for carrying out the present invention will be explained.

First Embodiment

Figure 2:
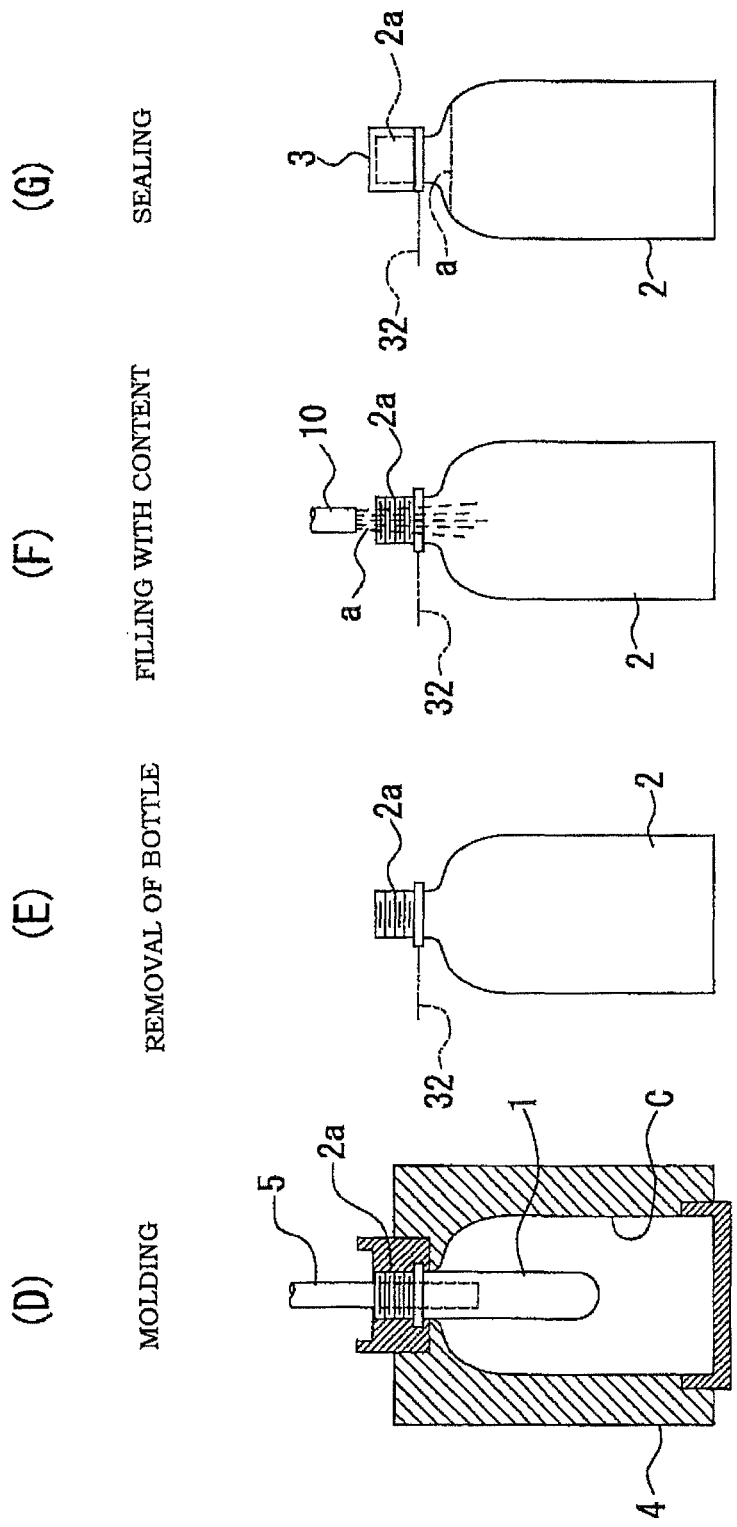
FIG. 2 includes (D), (E), (F) and (G) representing a molding process, a bottle take-out process, a content filling process, and a bottle sealing process, respectively, performed after the preform is sterilized.

According to this first embodiment, by sterilizing a preform, a bottle can be manufactured as sterilized one, the bottle can be filled with an aseptic drink, the bottle is then sealed with an a sterilized lid, and thereafter, the bottle is manufactured as finally packaged product such as shown in FIG. 2(G).

The packaged product is constructed with an aseptic (i.e., sterilized) bottle 2 and a cap 3 as a lid.

In this embodiment, although the bottle is made of PET (polyethylene terephthalate), the bottle is not limited to the PET, and it is made of a resin material such as polypropylene, polyethylene or like resin, and a re-cycled PET allocated resin may be also used. Further, a male screw (i.e., thread) is formed to a mouth portion 2a of the bottle 2.

The cap 3 is made up from a resin material such as polyethylene by an injection molding or like process or like, and a female (thread) portion is formed to an inner peripheral surface of the cap 3 at the same time for molding the cap 3.

The bottle 2 is filled up with drink "a" which has been preliminarily sterilized in a state that the interior of the bottle has been preliminarily sterilized. The cap 3 is applied to the mouth portion 2a of the bottle 2 after the filling of the drink "a", and then fastened and sealed thereto through screw-engagement between the male and female threads, thus completing a packaged product. The cap 3 is also preliminarily sterilized.

The bottle 2 is formed as a packaged product through the sterilizing process, the molding process, the drink filling process and the sealing process according to procedures described as following.

First, a preform 1 shown in FIG. 1(A) is continuously delivered at a predetermined speed.

The preform 1 is formed as a bottomed tubular member such as test tube by injection-molding the PET. The preform 1 is formed with a mouth like the mouth portion 2a of the bottle 2 shown in FIG. 2(G) at the initial time of the molding. The mouth portion 2a is also formed with a male thread at the same time of molding the preform 1.

As shown in FIG. 1(A), a sterilizer gas G or mist, or mixture thereof is supplied to the traveling preform 1.

In the present embodiment, although a hydrogen peroxide is used in the present embodiment as a sterilizer gas (sterilizing agent), another sterilizer or sterilizing agent is also usable.

As shown in FIG. 1(A), the preform 1 is blasted with the hydrogen peroxide gas G through a sterilizer supplying nozzle 6.

The hydrogen peroxide gas G is divided into two flows within the sterilizer supplying nozzle 6, and one of them is jetted toward inside the preform 1 and the other one is jetted toward an outer surface of the preform 1. After the hydrogen peroxide gas G is blasted through the sterilizer supplying nozzle 6, it flows into the preform in a state of gas, mist, or mixture thereof, or it flows in contact to the outer surface of the preform 1.

Further, an outside of the flow of the gas G jetted toward inside the preform is covered by an umbrella-shaped member 30. Although the gas G or mist flowing into the preform 1 leaks out of the mouth portion 2a of the preform 1, the flow of the leaking gas G or like collides with the umbrella-shaped member 30, is guided along the inner surface thereof, changes its flow direction towards the outer surface thereof, and contacts the outer surface of the preform 1.

The hydrogen peroxide gas G blasted to the preform 1 is generated by a sterilizer sterilizer gas generator 7, which will be explained hereinafter with reference to FIG. 4. The hydrogen peroxide gas G flows out of the sterilizer supplying nozzle 6, contacts the inner and outer surfaces of the preform 1.

The hydrogen peroxide gas G adheres to the surface of the preform 1 as a condensed film of hydrogen peroxide with a concentration of 35 percent by mass with a thickness of preferably 0.001 µL/cm$^2$ to 0.5 µL/cm$^2$. More preferably, the amount of the adhering hydrogen peroxide gas G ranges from 0.0024/cm$^2$ to 0.4 µL/cm$^2$.

Part of the hydrogen peroxide adhering to the surface of the preform 1 is adsorbed by the preform 1, and the remaining excess of the hydrogen peroxide remains on the surface of the preform 1.

Although not shown, the sterilizer supplying nozzle 6 may be located in a tunnel, and a gripper 32 (see FIG. 6) that conveys the preform 1 may be covered with a duct. In this way, the concentration of the hydrogen peroxide gas as the sterilizer in the tunnel can be increased, and the hydrogen peroxide gas can be condensed over the entire surface of the preform 1 introduced at room temperature.

Subsequently, as shown in FIG. 1(B), to the preform 1 supplied with the hydrogen peroxide, the hot air P is supplied from an air nozzle 80.

By blasting the hot air P, the remaining excess of the hydrogen peroxide is quickly removed from the surface of the preform 1.

Figure 7:
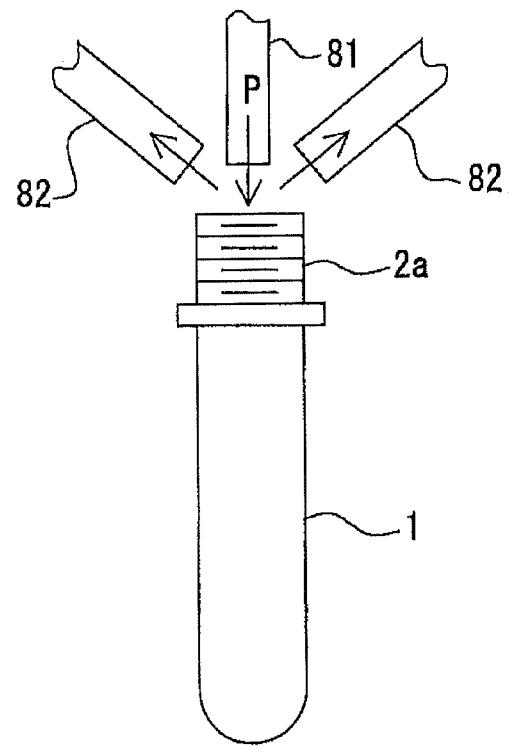
FIG. 7 is a view explaining a modified example showing hot air blasting process to the preform.

As shown in FIG. 1(B), the hot air P is blasted through a slit-shaped blasting port 80a formed to a box-shaped manifold 80b constituting the air nozzle 80, but the hot air P may be blasted from a tubular blasting nozzle 81 toward the preform 1 as shown in FIG. 7. Moreover, it may be possible to arrange a suction tube 82 near the blasting nozzle 81 so as to suck foreign substance or material such as dust exhausted outside from the preform 1 by the suction tube 82 at a time of blasting the hot air P from the tubular blasting nozzle 81 into the preform 1. As mentioned above, by recovering the foreign substance by the suction tube 82, the foreign substance can be prevented from mixing into the other preform or bottle formed thereafter.

Figure 8:
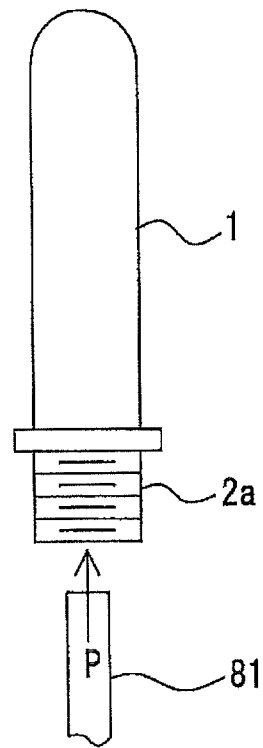
FIG. 8 is a view explaining another modified example showing hot air blasting process to the preform.

Further, as shown in FIG. 8, it may be possible to dispose the blasting nozzle 81 blasting the hot air P with an opening directed upward and with the preform in the inverted state, in which the hot air P is blasted into the preform 1 through the mouth portion 2a from the lower side of the blasting nozzle 81 of the inverted preform 1. According to such arrangement, the foreign substance existing inside the preform 1 can be removed from the preform 1 by blasting air under pressure through the mouth portion 2a as well as self-gravity thereof.

As shown in FIG. 1(C), the sterilized preform 1 is heated by an infrared heater 18a or other heating means to a temperature suitable for the blow-molding process which will be performed to a temperature of about 90 to 130° C.

Further, a temperature for heating the mouth portion 2a of the preform 1 is suppressed to a temperature less than 70° C. for preventing deformation or like of the preform.

In such heating process as mentioned above, the preform 1 is, and it is desirable, as shown in FIG. 1(C), conveyed while rotating together with the spindle (mandrel) in a suspended upstand state (or upside down state) by inserting a spindle (or mandrel) 43 into the mouth portion 2a. Thus, the preform 1 can be evenly heated by the infrared heater 18a.

It may be possible to insert the mandrel in place of the spindle 43 into the preform 1 so as to convey the preform while rotating in the inverted (upside down) state.

By heating the preform with the infrared heater 18a, the hydrogen peroxide adsorbed by the preform 1 is activated and sterilizes bacteria on the preform 1.

The heated preform 1, as shown in FIG. 2(D), is blow-molded into the bottle 2 within the mold 4.

The mold 4 for the blow-molding is continuously the mold traveled at the same speed as the traveling speed of the preform, and is then clamped (mold-clamped). Thereafter, the mold 4 is opened after the blow-molding process is performed to the preform 1 within the mold 4.

As mentioned above, the preform 1 is entirely, except its mouth portion 2a, uniformly heated to a temperature suitable for the heating process shown in FIG. 1(C), the thus heated preform 1 is placed and set in the mold 4 as shown in FIG. 1(D), and an extension rod (not shown) is inserted into the preform 1 through a center hole of the blow nozzle 5.

During the traveling of the mold 4, the preform 1 is expanded into the bottle 2 as final product within a cavity C of the mold 4 by sequentially blasting aseptic air, for example, for primary blow-molding and for secondary blow-molding from the blow nozzle 5 into the preform 1.

When the bottle 2 has been molded in the mold 4, the mold 4 is opened while being traveled, and the final product of the bottle 2 is taken out of the mold as shown in FIG. 2(E).

The bottle 2 taken out of the mold 4 is filled up with the drink "a" through the filling nozzle 10 as shown in FIG. 2(F), and subsequently, as shown in FIG. 2(G), the cap 3 as a lid is applied to the bottle 2.

Further, the drink "a" may fill the bottle 2 at a normal temperature under an aseptic environment after the sterilizing treatment subjected to the drink itself.

Otherwise, as shown in the following Table 1, the drink "a" may fill the bottle 2 at a medium temperature such as 60 to 75° C.

In a case of no use of a pasteurizer or a pasteu-cooler, sufficient sterilizing effect can be obtained by filling the bottle 2 at a temperature of more than 70° C. in an assumption of an outside temperature of 3° C.

On the other hand, in a case of use of a pasteurizer or a pasteu-cooler, a predetermined desirable sterilizing effect against mold spore can be obtained by treating the temperature of the pasteurizer for 5 to 10 minutes at a temperature of more than 60 to 65° C.

Further, in a case when the drink temperature at the filling time is more than 75° C., although the sufficient sterilizing effect can be obtained, if the bottle is made of PET, there is a fear such that the bottle is deformed except a case of a heat-resisting PET bottle, so that a test was conducted at temperatures under 75° C.

TABLE 1

| | IN PRESENCE OF PASTEURIZER OR PASTER-COOLER | | | | IN ABSENCE OF PASTERRIZER |
|---|---|---|---|---|---|
| | TEMPERATURE OF HOT WATER SHOWER 65.0° C. | | TEMPERATURE OF HOT WATER SHOWER 60.0° C. | | OR PASTEU-COOLER (IN 3° C. |
| TEMPERATURE OF DRINK AT FILLING | SHOWER DURATION 10 min | SHOWER DURATION 5 min | SHOWER DURATION 10 min | SHOWER DURATION 5 min | CONSTANT TEMPERATURE CHAMBER) |
| 75.0° C. | — | — | — | — | ○ |
| 72.5° C. | — | — | — | — | ○ |
| 70.0° C. | — | — | — | ○ | ○ |
| 65.0° C. | — | ○ | ○ | Δ | X |
| 60.0° C. | — | ○ | Δ | X | — |
| 55.0° C. | — | X | X | X | — |

Further, in the above Table 1, [○] represents a case of sterilizing effect of more than 6.0 Log, [Δ] represents a case of sterilizing effect of 5.5 Log to 6.0 Log, and [x] represents a case of sterilizing effect of less than 5.0 Log.

The above test was conducted for the purpose of obtaining a condition for a filling temperature of drink which can achieve the sterilizing effect of more than 6.0 Log with respect to fungus (mold) of *A. niger* NBRC6341 as to a bottle inner surface and a cap inner surface. Further, although another fungus having a heat resisting property more than that of this fungus exists, in view of the sterilizing effect to the preform by chemical agent sterilization and the sterilizing effect to the chamber by SOP treatment, it is considered that commercially suitable aseptic filling operation may be performed by ensuring the sterilizing effect of 6 Log.

The test was conducted in a condition such that a hot water filled a fungus adhering bottle, an inverted sterilization was performed for 30 seconds after the filling, and subsequently, the filled water was filtrated by a filter and then cultivated. Thereafter, liquid culture medium was mixed and diluted, and was then separately cultivated.

In the filling case at the medium temperature, although the remaining of spore fungus in the drink "a" or bottle 2 is permitted, mold, yeast or like fungus is sterilized by the heat of the drink "a", and the deformation of the PET bottle 2 is not permitted to be deformed. Accordingly, the case of the middle temperature filling treatment is suitable for acidic drink, carbonated drink, mineral water, which have the nature of suppressing germination of spore fungus, or neutral drink which is proven to a hot bag.

The aseptic filling system for performing the sterilizing treatment to the preform as mentioned above is constructed as one shown in FIG. 3, for example.

Figure 3:
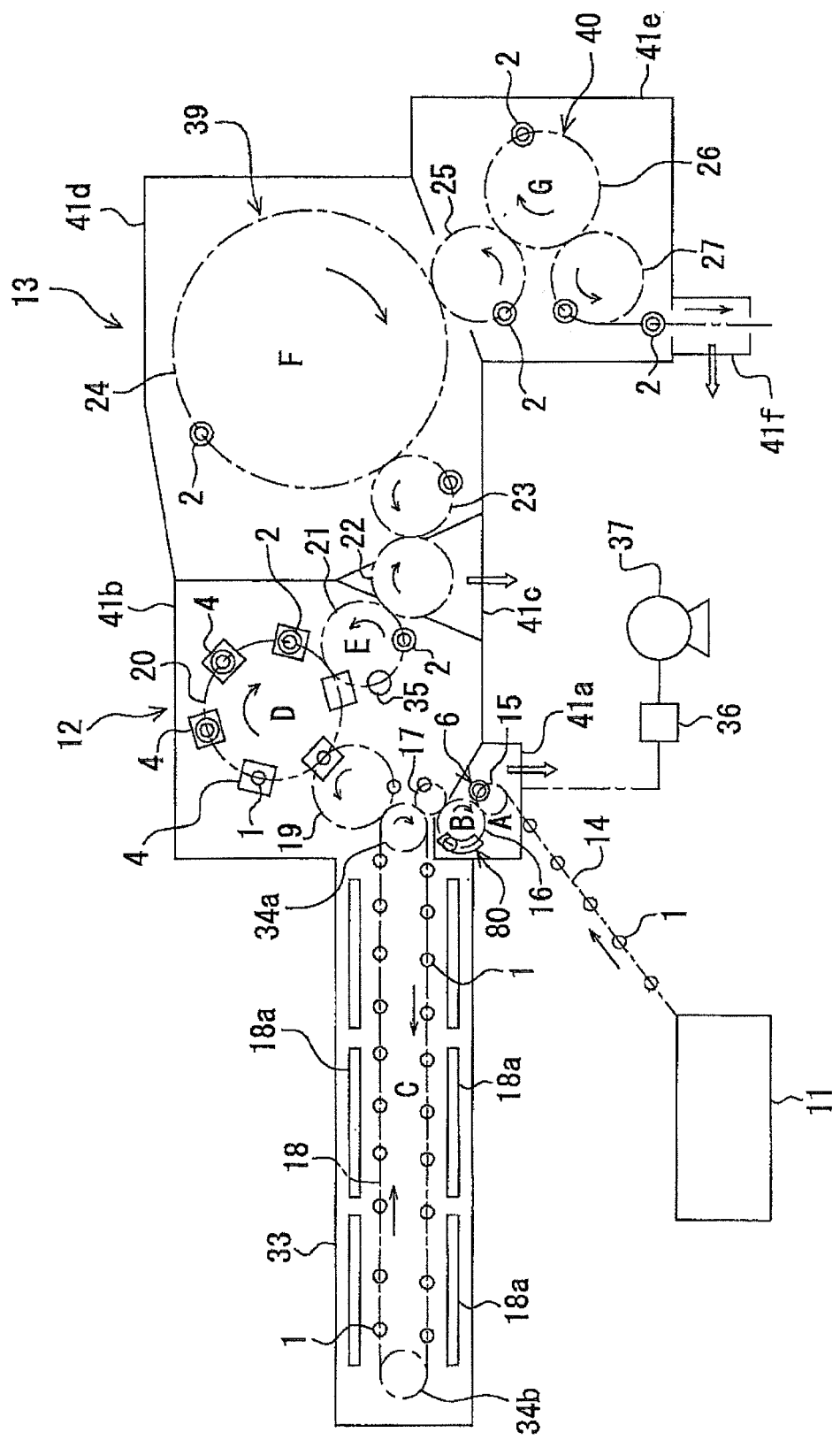
FIG. 3 is a plan view schematically illustrating one example of an aseptic filling system equipped with a bottle sterilizing apparatus according to the present invention.

As shown in FIG. 3, the aseptic filling system includes a preform supply machine 11 for sequentially supplying preforms 1, each having a bottomed tubular shape, a blow-molding machine 12, and a filling machine 13 for filling a molded bottle 2 with the drink "a" and sealing the same with a cap 3 (see FIG. 2(G)).

The aseptic filling system is surrounded by chambers 41a, 41b, 41c and 41d at several portions on the way between the blow-molding machine 12 and the filling machine 13. The chamber 41b may be mere a frame structure such as shroud with no sealing structure.

Further, it is possible to manufacture a bottle having high aseptic condition level by sterilizing the chamber 41b before the manufacture of a package and supplying positive pressure passing through an HEPA filter into the chamber 41b to thereby maintain the aseptic condition in the chamber 41b. As one of such sterilizing method, the interior of the chamber 41b may be sterilized by the hydrogen peroxide gas of less than 10 mg/L, or portions to which the preform 1 and the bottle 2 contact may be irradiated with a UV lamp (for ultraviolet ray sterilization). Furthermore, portions, to which a mold, an extension rod, a gripper and the like contact, may be wiped up with a chemical agent containing 1% by mass of ethanol or hydrogen peroxide.

A preform conveying means, a mold conveying means and a bottle conveying means are located on the way between the preform supplying machine 11 and the filling machine 13, in which the mold conveying means is for conveying the preforms 1 on the first conveying path, the mold conveying means is for conveying the mold 4 having a cavity "C" having a shape corresponding a final product of the bottle 2 (see FIG. 2(D)) on the second conveying path connected to the first conveying path, and the bottle conveying means is for conveying the bottle 2 molded by the mold 4 on the third conveying path connected to the second conveying path.

The first conveying path for the preform conveying means, the second conveying path for the mold conveying means and the third conveying path for the bottle conveying means are communicated with each other, and the grippers and like members, not shown, for holding and conveying the preforms 1 and the bottles 2 are provided on these conveying paths.

The preform conveying means is provided, on its first conveying path, with a preform conveyer 14 for subsequently conveying the preforms 1 at a predetermined interval. The preform conveying means is further provided with a line (train) of wheels 15, 16, 17 which receive the preforms 1 from the terminal end of the conveyer 14, and an endless chain 18 which receives the preforms 1 and then conveys the preforms 1.

A sterilizer sterilizer gas generator 7 generating the hydrogen peroxide gas G and a sterilizer supplying nozzle 6 for discharging the hydrogen peroxide gas G toward the preform 1 are located on predetermined positions on the traveling path of the preform 1 in the wheel 15.

Figure 4:
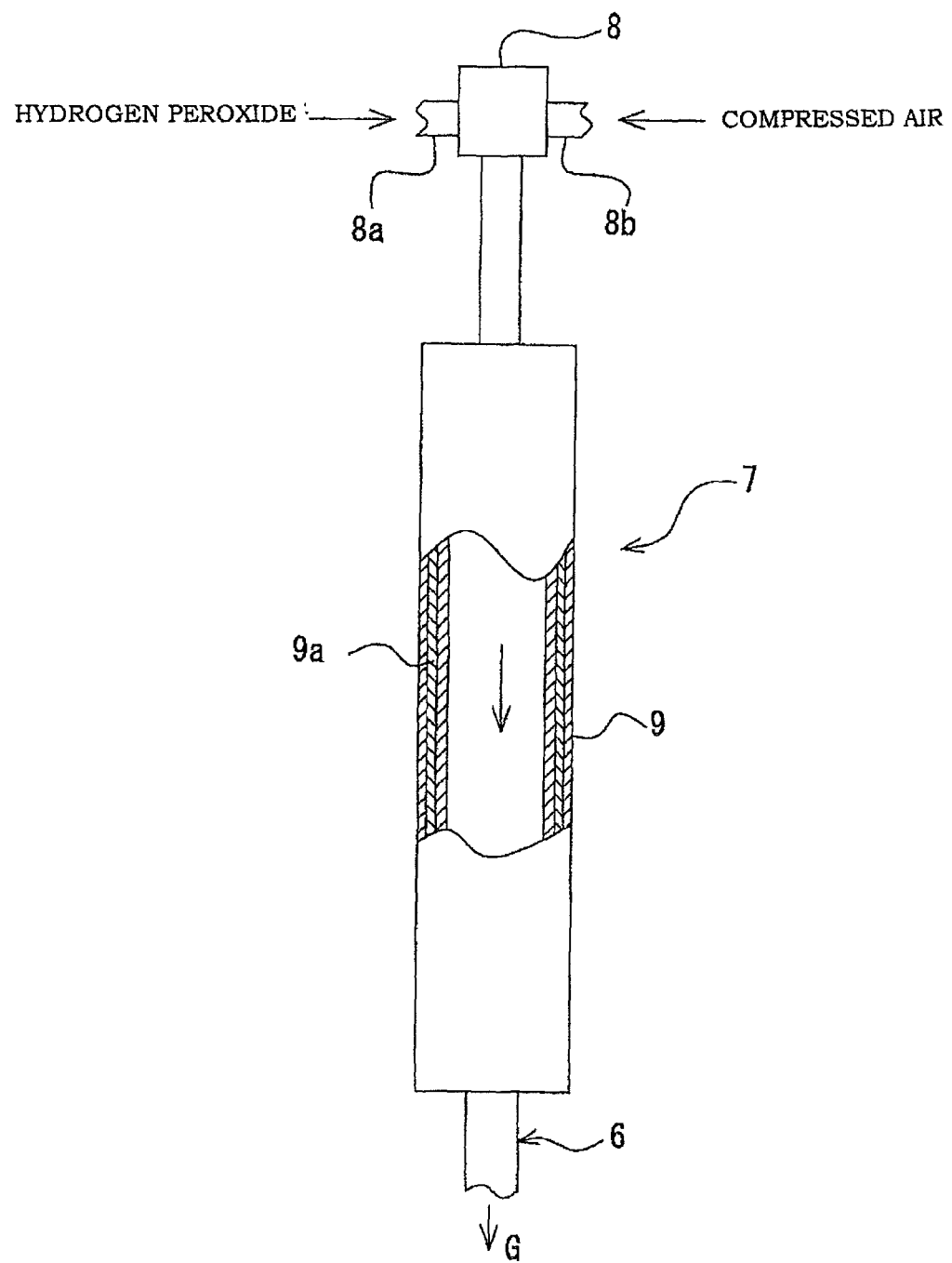
FIG. 4 is a vertical sectional view illustrating one example of a sterilizing gas generator for generating a hydrogen peroxide gas.

As shown in FIG. 4, the sterilizer sterilizer gas generator 7 is provided with a hydrogen peroxide supplying portion 8 constructed as a twin-fluid spray nozzle for supplying the solution of the hydrogen peroxide as the sterilizer in form of liquid drops and an evaporating portion (evaporator) 9 for evaporating the hydrogen peroxide by heating the mist of the hydrogen peroxide supplied from the hydrogen peroxide supplying portion 8 to a temperature more than its boiling point and less than its non-degradable temperature. The hydrogen peroxide supplying portion 8 has a structure in which the hydrogen peroxide solution from a hydrogen peroxide supply path 8a and compressed air from a compressed air supply path 8b respectively introduced into the hydrogen peroxide supplying portion 8 are then atomized into the evaporating portion 9. The evaporating portion 9 is in form of a pipe with a heater 9a interposed between inner and outer wall portions thereof, and the hydrogen peroxide mist sprayed into this pipe is heated and then evaporated. The evaporated hydrogen peroxide gas is jetted outward of the evaporating portion 9 through the hydrogen peroxide supply nozzle 6.

Figure 6:
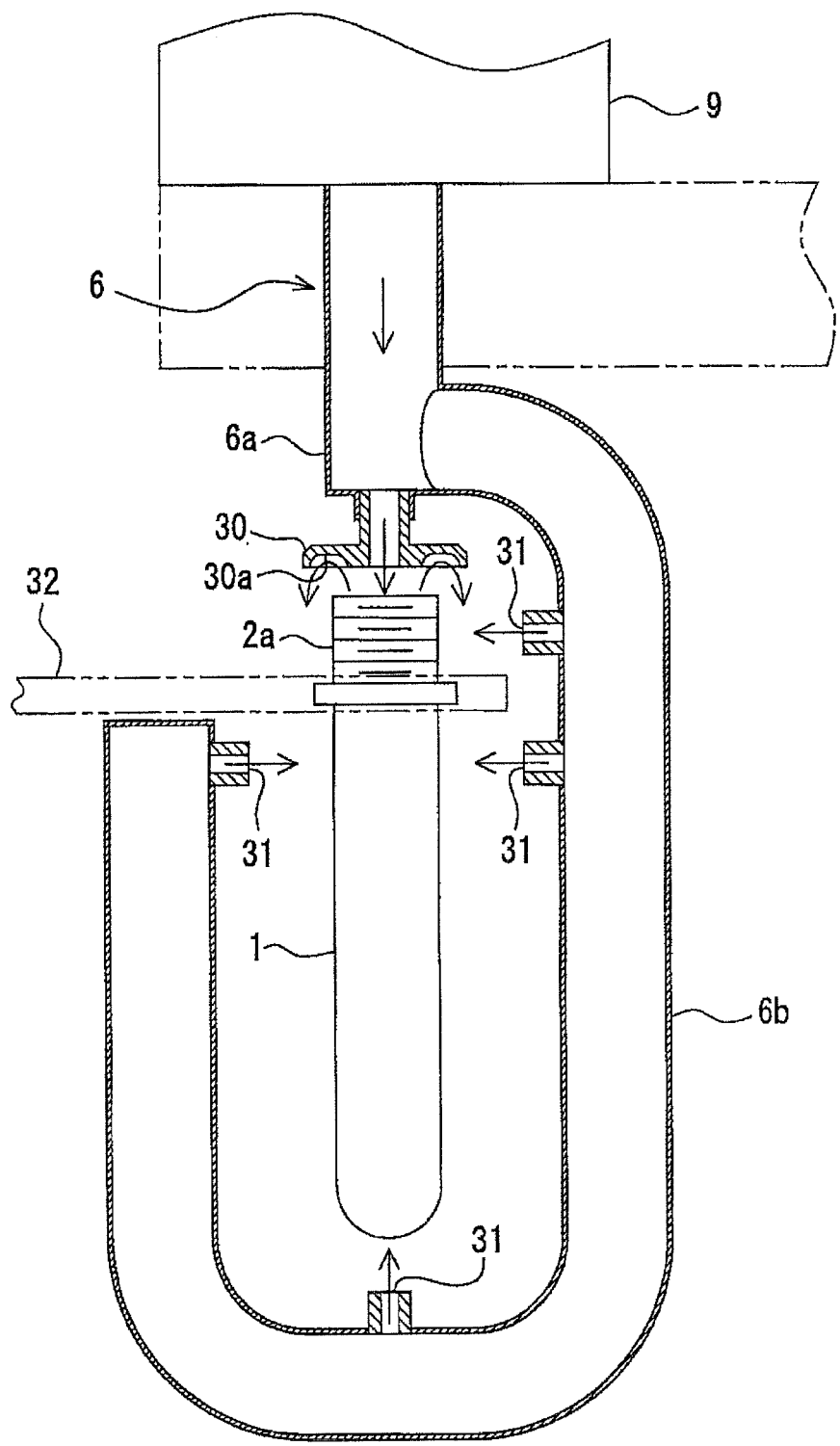
FIG. 6 is a vertical sectional view illustrating a hydrogen peroxide supply nozzle incorporated in the bottle sterilizing apparatus according to the present invention.

As shown in FIG. 6, the sterilizer supply nozzle 6 is branched into a plurality of pipe lines 6a, 6b for sending the hydrogen peroxide gas G.

The pipe line 6a among the plural pipe lines 6a, 6b has a discharge port facing an opening of the mouth portion 2a of the preform 1. The hydrogen peroxide gas G generated by the sterilizer sterilizer gas generator 7 is blasted toward the preform 1 from the discharge port of the pipe line 6a of the sterilizer supply nozzle 6 in form of gas G or mist, or mixture thereof, and flows into the preform 1. In this manner, the hydrogen peroxide adheres to the inner surface of the preform 1.

Further, by supplying hot air, as aseptic air, into the sterilizer supply nozzle 6, the pipe lines 6a, 6b and others from middle portions thereof, dew condensation of the hydrogen peroxide solution in these pipe lines may be prevented. Such dew condensation may also be prevented by winding electric ribbon heater around the pipe lines 6a, 6b and the others.

It is preferred that a portion around the discharge port of the pipe line 6a is covered with an umbrella-shaped member 30, which has a lower surface in which an annular groove 30a having approximately semi-circular section is formed. The hydrogen peroxide gas G or mist, or their mixture flowing into the preform 1 through the discharge port of the pipe line 6a fills the preform 1, and thereafter, leaks outward. However, the leaked hydrogen peroxide gas G or mist, or their mixture is guided to the outer surface of the preform 1 by the lower surface of the umbrella-shaped member 30 and the annular groove 30a and then flows outward along the outer surface of the preform 1. Accordingly, the hydrogen peroxide leaking from the pipe line 6a also adheres to the outer surface of the preform 1.

On the other hand, the other pipe line 6b is formed so as to extend in an approximately U-shape along the outer surface of the preform 1, and a discharge port 31 of this pipe line 6b faces the outer surface of the preform 1. The hydrogen peroxide gas G generated by the sterilizer sterilizer gas generator 7 is jetted toward the outer surface of the preform also from the discharge port 31 of the other pipe line 6b, and the thus formed hydrogen peroxide gas G or mist, or their mixture is blasted to the outer surface of the preform 1. The blasted hydrogen peroxide from the pipe line 6a is mixed with the hydrogen peroxide leaking from the mouth portion 2a of the preform 1 and adheres to the outer surface of the preform, thereby sterilizing bacteria and the like fungus adhering to the outer surface of the preform 1.

The amount of the hydrogen peroxide solution to be blasted to the inner and outer surfaces of the preform 1 can be adjusted by respectively adjusting the inner diameter of the discharge port 31 of the pipe line 6a for supplying the gas G to the inner surface of the preform 1, the inner diameter of the discharge port 31 of the pipe line 6b, the number of the discharge ports and the like.

In FIG. 6, reference numeral 32 denotes a gripper disposed around the wheel 15 that conveys the preform 1.

An air nozzle 80 (FIG. 1(B)) is disposed on the traveling path of the preform 1 in the wheel 16, the air nozzle 80 acting to activate the hydrogen peroxide adhering to the inner and outer surfaces of the preform 1 by discharging the hot air P toward the preform 1 to thereby discharge the activated hydrogen peroxide externally of the preform 1.

As shown in FIG. 5(A), the air nozzle 80 has a box-shaped manifold 80b bent along a circular arc of the wheel 16, and the blasting port 80a in form of slit is formed in the bottom surface of the manifold 80b. The air nozzle 80 is located above the wheel 16 so that the blasting port 80a of the air nozzle 80 extends along the traveling path of the preform 1 in the wheel 18. Furthermore, as sown in FIG. 5(B), a blower 76, an HEPA filter 77, and an electric heater 78 are connected in series to the manifold 80b. Outside air taken by the blower 76 is sterilized by the HEPA filter 77 and then heated by the electric heater 78 to generate the hot air P which is then send into the air nozzle 80.

Air to be supplied to the air nozzle 80 may be a compressed air which has a high propelling force and is sterilized by an aseptic filter without using the air from the blower 76. Moreover, a highly pressurized air using for blow-molding in the blow molding machine 12 may be re-used by being recovered.

The hot air P supplied into the manifold 80b of the air nozzle 80 is jetted from the blasting port 80a, flows toward the preform 1 traveling under the blasting port 80a with the mouth portion 2a thereof being directed upward, and a part of the hot air P flows into a hollow interior of the preform 1 and the other part thereof flows along the outer surface of the preform 1.

By blasting the hot air P, the remaining excess of the hydrogen peroxide is removed from the inner and outer surfaces of the preform 1 and prevented from being introduced into the heating furnace 50 in the subsequent step.

Further, the foreign substance removing percentage or ratio can be increased by arranging a suction tube 82 as shown in FIG. 7 and inverting the nozzle 81 and the preform 1 as shown in FIG. 8.

Figure 9:
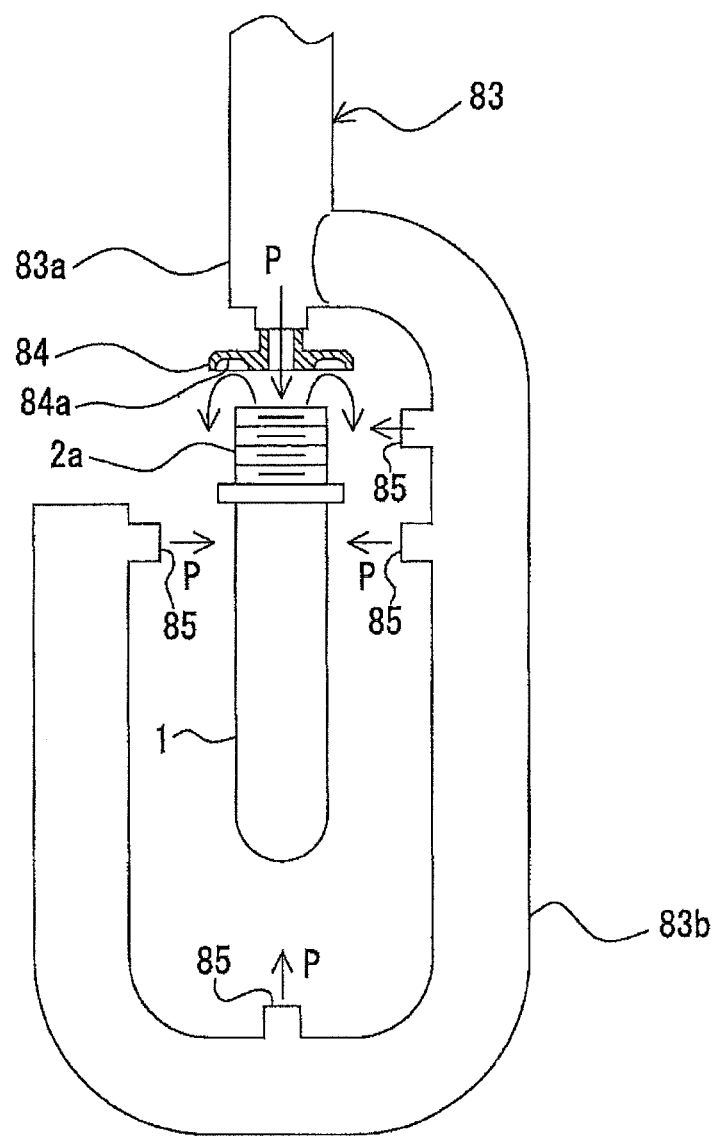
FIG. 9 is a view explaining a further modified example showing hot air blasting process to the preform.

The supply of the hot air P may be performed by using an air nozzle 83 shown in FIG. 9. The air nozzle 83 has a structure similar to that of the sterilizer supply nozzle shown in FIG. 6. In FIG. 9, reference numerals 83a and 83b denote a plurality of blanched pipe lines for sending the hot air P, in which a discharge port of one pipe line 83a faces the opening of the mouth portion 2a of the preform. The hot air P is jetted from the discharge port of the pipe line 83a toward the preform 1 and flows into the preform 1. As a result, the hydrogen peroxide adhering to the inner surface of the preform 1 is activated and the surplus hydrogen peroxide is removed.

Reference numeral 84 denotes an umbrella-shaped member covering the periphery of the discharge port of the pipe line 83a, and an annular groove 84a having approximately semi-circular sectional shape is formed in the lower surface of the umbrella-shaped member 84. The hot air P introduced into the preform 1 from the discharge port of the pipe line 83a fills the interior of the preform 1, and then, leaks from the mouth portion 2a of the preform 1. The leaking hot air P is guided to the outer surface of the preform 1 by the lower surface of the umbrella-shaped member 84 and the annular groove 84a and flows along the outer surface of the preform 1 so that the hot air P leaking from the pipe line 83a also contacts the outer surface of the preform 1.

On the other hand, the other pipe line 83b is formed so as to extend in an approximately U-shape along the outer surface of the preform 1, and a discharge port 85 of this pipe line 83b faces the outer surface of the preform 1. The hot air P is jetted toward the outer surface of the preform 1 also from the discharge port 85 of the other pipe line 83b and contacts the outer surface of the preform 1. As a result, the hot air P from the pipe line 83a is mixed with the hot air P leaking from the mouth portion 2a of the preform 1 and adheres to the outer surface of the preform 1. Then, the surplus hydrogen peroxide adhering to the outer surface of the preform 1 is removed.

As shown in FIG. 3, the wheels 15 and 16 are surrounded by the chamber 14a, to which exhaust means composed of a filter 36 for filtrating the air inside the chamber 41a and a blower 37 is connected. According to such connection, the surplus hydrogen peroxide discharged from the sterilizer supply nozzle 6 is removed by the filter 36 of the exhaust means, and thereafter, is discharged outside the chamber 41a. Thus, the flow-in of the hydrogen peroxide into the adjacent blow-molding machine 12 can be prevented. It is preferred to adjust the supply amount into or exhaust amount from the chamber 41a so as to create a negative pressure in the chamber 41a lower than atmospheric pressure.

Further, bacteria or like fungus may be prevented from invading into the chamber 41a now under negative pressure by locating the chamber 41a, the heating furnace 33, the chamber 41b and so on within a clean room, not shown, such as chamber 41b.

The endless chain 18 is disposed as the conveying path of the preforms 1 within the heating furnace 33 provided with the infrared heater 18a described above. A number of spindles 43 shown in FIG. 1(C) ate attached to the endless chain 18 at a constant pitch. Each spindle 43 can rotate while traveling together with the traveling of the endless chain 18. Into the mouth portion 2a of the preform 1 delivered to the endless chain (18) side from the wheel (17) side, the spindle 43 is inserted as shown in FIG. 1(C), so that the preform 1 can be kept in its positively standing attitude. It may be further possible to convey the preform in the standing attitude as shown in FIG. 8 by replacing the spindle with a mandrel.

The heating furnace 33 is provided with a furnace chamber extending in one direction. Inside the furnace chamber, the endless chamber 18 is stretched between a pair of pulleys 34a and 34b opposing to each other in a horizontal plane. The endless chain 18 and associated members constitute an endless conveyer for conveying a number of the preforms 1 in a suspended attitude. The infrared heaters 18a are attached to the inner peripheral wall of the furnace chamber along the outward path and return path of the traveling of the endless chain 18.

When the preform 1 is received by the spindle 43 through the preform conveyer 14 and the row of the wheels 15, 16 and 17, the preform 1 rotates and travels along the inner wall surface of the heating furnace 33. The infrared heaters 18a are attached throughout the inner wall surface of the heating furnace 33, so that the preform 1 conveyed by the spindle 43 is heated by these infrared heaters 18a. The preform 1 rotates in the heating furnace 33 together with the rotation of the spindle while being evenly heated by the infrared heaters 18a, and portions other than the mouth portion 2a of the preform 1 are heated up to a temperature 90° C. to 130° C. suitable for the blow-molding. The heating temperature to the mouth portion 2a is regulated to less than 70° C. so as not to damage the sealing performance and not to deform the preform 1 when the cap is applied to the mouth portion 2a.

The blow-molding machine 12 is provided with several sets of the mold 4 and the blow nozzle 5 (FIG. 2(D)) for receiving the preform heated by the infrared heater 18a of the preform supplying machine 11 and then molding the preform 1 into the bottle 2.

As shown in FIG. 3, the second conveying path of the mold conveying means is located within the blow-molding machine 12. The second conveying path is composed of a line of wheels 19, 20, 21 and 22.

A plurality of molds 4 and blow nozzle 5 are located around the wheel 20, and turn around the wheel 20 at a constant speed together with the wheel 20.

When the gripper, not shown, of the wheel 19 receives the preform 1 heated in the heating furnace 33 of the preform supplying machine 11 and then transfers the preform 1 to the mold 4 located around the wheel 20, the mold 4 now being opened in two mold halves is closed to thereby grip the preform 1 such as shown in FIG. 2(D). The preform 1 in the mold 4 is blown with highly pressurized air through an aseptic filter for blow-molding from a blow nozzle 5 while being rotated around the wheel 20 together with the mold 4 and the blow nozzle 5, thereby being molded into a final product of a bottle 2. As shown in FIG. 1(C), since the preform 1 is heated evenly to a predetermined temperature within the heating furnace 33, the blow-molding process can be smoothly performed.

Furthermore, as described above, the hydrogen peroxide adhering to each preform 1 is removed from the preform 1 before the entrance into the heating furnace 33 by blowing the hot air P. Accordingly, the seal member and other components or members located inside the blow-molding machine 12 becomes free from any damage by the adhesion of the hydrogen peroxide. Moreover, whitening (bleaching), distortion, uneven molding, or like defect to the bottle 2 resulted from the adhesion of the hydrogen peroxide can be prevented from causing.

When the preform 1 closely contacts the inner surface of the cavity C of the mold 4 to thereby form the bottle 2, the mold is opened at an instance contacting the wheel 21, and the bottle 2 is received by the gripper, not shown, of the wheel 21.

The bottle 2 reaching the wheel 21 from the blow-molding machine 12 is inspected whether it is defective or not in the molded performance by an inspection device 35 arranged on the outer periphery of the wheel 21. The inspection device 35 may be provided with a light source and a camera for inspecting the top surface of the mouth portion 2a of the molded bottle 2 is made to be flat or not.

The inspected bottle 2, which is judged to be defective, is rejected from the conveying path by a rejection device, not shown, and only an acceptable product is conveyed to the wheel 22.

The filling machine 13 is provided therein with the third conveying path as bottle conveying means, and such third conveying path is equipped with a line (train) of wheels 23, 24, 25, 26 and 27.

Around the outer periphery of the wheel 24, a number of filling nozzles 10 for filling the aseptic bottles 2 with the drink "a" are located so as to constitute a filler 39, and around the wheel 26, a capper 40 for applying the cap 3 (FIG. 2(G)) is also constituted to thereby seal each of the bottles 2 filled up with the drink "a".

Since conventionally known filler and capper may be usable as such filler 39 and capper 40, detailed descriptions thereof will be omitted herein.

The chamber 41c is located so as to surround the wheel 22, and this chamber 41c functions as surrounding air shut-off chamber for shut off surrounding (atmosphere) air existing between the chamber 41b and the chamber 41d. Exhaust means like that composed of the filter 36 and the blower 37 and connected to the chamber 41a shown in FIG. 3 is connected to this chamber 41c to thereby exhaust outward the inner air in the chamber 41d. Thus, gas or mist of the sterilizer and the cleaner generated within the chamber 41d is rejected outside the chamber 41c by performing the COP (Cleaning Out of Place) with respect to the interior of the chamber 41d of the filling machine 13, and to thereby prevent the mist or line from flowing into the chamber 41b of the blow-molding machine 12.

Hereunder, operation and/or function of the drink filling machine will be explained with reference to FIGS. 1 to 8.

First, the preforms 1 are conveyed toward the heating furnace 33 by the preform conveyer 14 and the line of the wheels 15, 16, 17.

At the time when the preforms 1 travel around the wheel 15 before the entering into the heating furnace 33, the hydrogen peroxide gas G or mist, or their mixture is supplied toward the preforms 1 from the sterilizer supplying nozzles 6, respectively.

Part of the hydrogen peroxide supplied from the sterilizer supplying nozzle 6 is adsorbed by the preform 1, and the remaining excess of the hydrogen peroxide remains on the surface of the preform 1.

Sequentially, the hot air P is blasted from the air nozzle 80 to the preform 1 at the time when the preform adhered with the hydrogen peroxide travels around the wheel 16. By the blasting of the hot air P, the remaining excess of the hydrogen peroxide is quickly removed from the surface of the preform 1.

As shown in FIG. 7, the hot air P may be blasted into the preform 1 through the air nozzle 81 to blow away foreign matters from inside the preform 1, and the foreign matters blown away may be collected through the suction tube 82. Alternatively, as shown in FIG. 8, the air nozzle 81 and the preform 1 may be inverted from the position shown in FIG. 7 so that foreign matters in the preform 1 can be easily removed to outside the preform 1.

Thereafter, the preform 1 is received by the spindle 43 above the endless chain 18 and then conveyed into the heating furnace 33.

The preform 1 in the heating furnace 33 is heated by the infrared heater 18a to thereby evenly heat the entire of the preform, except the mouth portion 2a, to a temperature suitable for the blow molding treatment.

By the heating, the hydrogen peroxide adsorbed by the preform 1 is activated and sterilizes bacteria on the preform 1.

When the preform 1 heated in the heating furnace 33 and sterilized at the same time travels around the outer periphery of the wheel 20, the preform 1 is held by the mold 4 as shown in FIG. 2(D), and aseptic highly-pressurized air is blasted through the blow nozzle 5, and then, the preform 1 is expanded as a product bottle 2 within the cavity C of the mold 4.

The thus molded bottle 2 is taken out of the mold 4 after opening the mold 4 by the gripper of the wheel 21, and the bottle 2 is then inspected by the inspection device as to whether it is defective product or not.

Thereafter, the defective bottle 2 is rejected outward from the traveling line of the bottles by a rejecting device, not shown, and only a non-defective bottle 2 is guided and travels into the filling machine while being transferred to the line of the wheels 22, 23, 24, 25, 26 and 27.

Within the filling machine 13, the sterilized drink "a" fills the bottle 2 by the filling nozzle 10 of the filler 39 as shown in FIG. 2(F). The bottle 2 filled up with the drink "a" is applied with the cap 3 by the capper 40 to be sealed (see FIG. 2(G)), and discharged through the outlet port of the chamber 41d.

As described hereinbefore, since, the filler 39 and the capper 40 are known ones, detailed descriptions thereof will be omitted herein.

Further, the interior of the chamber 41d of the aseptic filling machine 13 is sterilized (SOP) by scattering the hydrogen peroxide gas or peracetic acid solution before production of package. Then, after the sterilization, by supplying the air through the aseptic filter, the interior of the chamber 41d can be kept at positive pressure. As a result, although the air and the like in the chamber 41d tends to flow toward the side of the blow-molding machine 12, since the surrounding air shut-off chamber 41c is positioned between both the cambers 41b and 41d and such air and the like are discharged outward therefrom, high-humid air in the filling area of the chamber 41d can be properly prevented from entering into the molding area in the chamber 41b.

It may be possible to locate or arrange other various equipments and the like such as the sterilizer supply nozzle 6 and the air nozzle 80 for sterilizing the preform 1 for the sterilization of the bottle 2 to the portions of the wheels 22 and 23. In such case, since the sterilizer is exhausted outward from the surrounding air shut-off chamber 41c by the exhausting means in the surrounding air shut-off chamber 41c, the sterilizer can be shut off from flowing toward the side of the blow-molding machine 12.

Second Embodiment

According to the second embodiment, steps shown in FIGS. 10(A) and 10(B) are used instead of the steps shown in FIGS. 1(A) and 1(B).

As shown in FIG. 10(A), first, a drop Q of a solution of hydrogen peroxide as the sterilizer is dripped into the preform 1 through the mouth portion 2A. The amount of drops Q falls within the maximum amount of hydrogen peroxide that can be adsorbed by one preform 1.

As shown in FIG. 10(B), a large number of preforms 1 containing drops of hydrogen peroxide are put in a container 86 and sealed. More specifically, a sealed bag 87 is put in the rigid container 86, a large number of preforms 1 are put in the sealed bag 87, the sealed bag 87 is sealed, and then the container 86 is covered with a lid 86a. Aging occurs in the container for a predetermined time, and the hydrogen peroxide supplied into the preforms is adsorbed by the preforms 1.

The place where the aging is not limited to the interior of the sealed bag 87, and the aging can occur in any sealed chamber.

Figure 1:
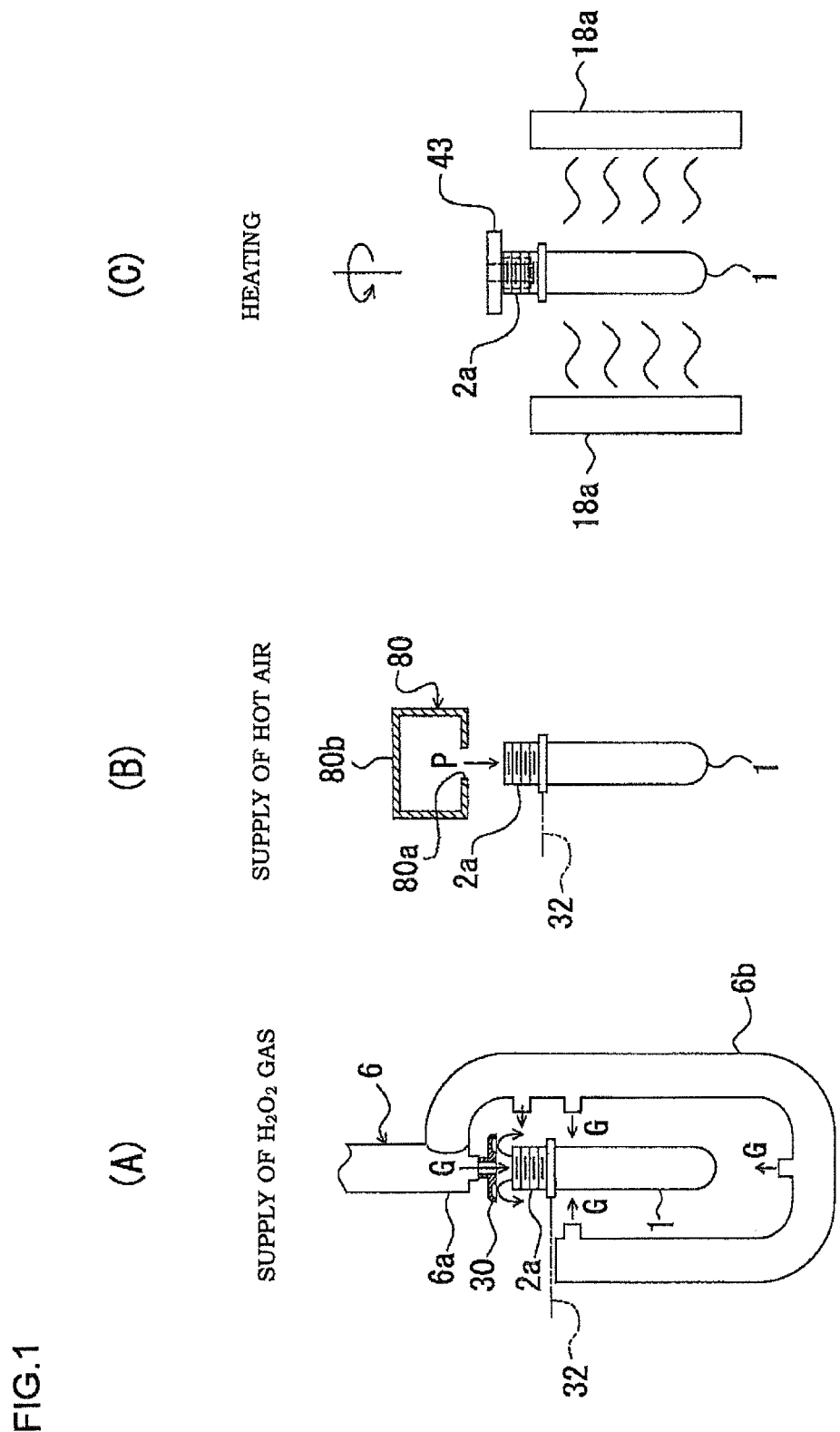
FIG. 1 represents a bottle sterilizing method according to a first embodiment of the present invention, in which (A) and (B) show steps of the bottle sterilizing method according to the present invention, and (C) shows a heating step performed after a preform is sterilized.

After the aging, the sealed bag 87 is opened, and the preforms 1 are removed from the sealed bag 87 and heated to a blow-molding temperature as shown in FIG. 1(C). After that, the preforms 1 are molded into packaged products through the steps shown in FIGS. 1(D) to 2(G).

Third Embodiment

According to the third embodiment, an aseptic package provided with a bottle 2 and a cap 3 such as shown in FIG. 14(K) can be manufactured as in the case of the first embodiment.

Figure 11:
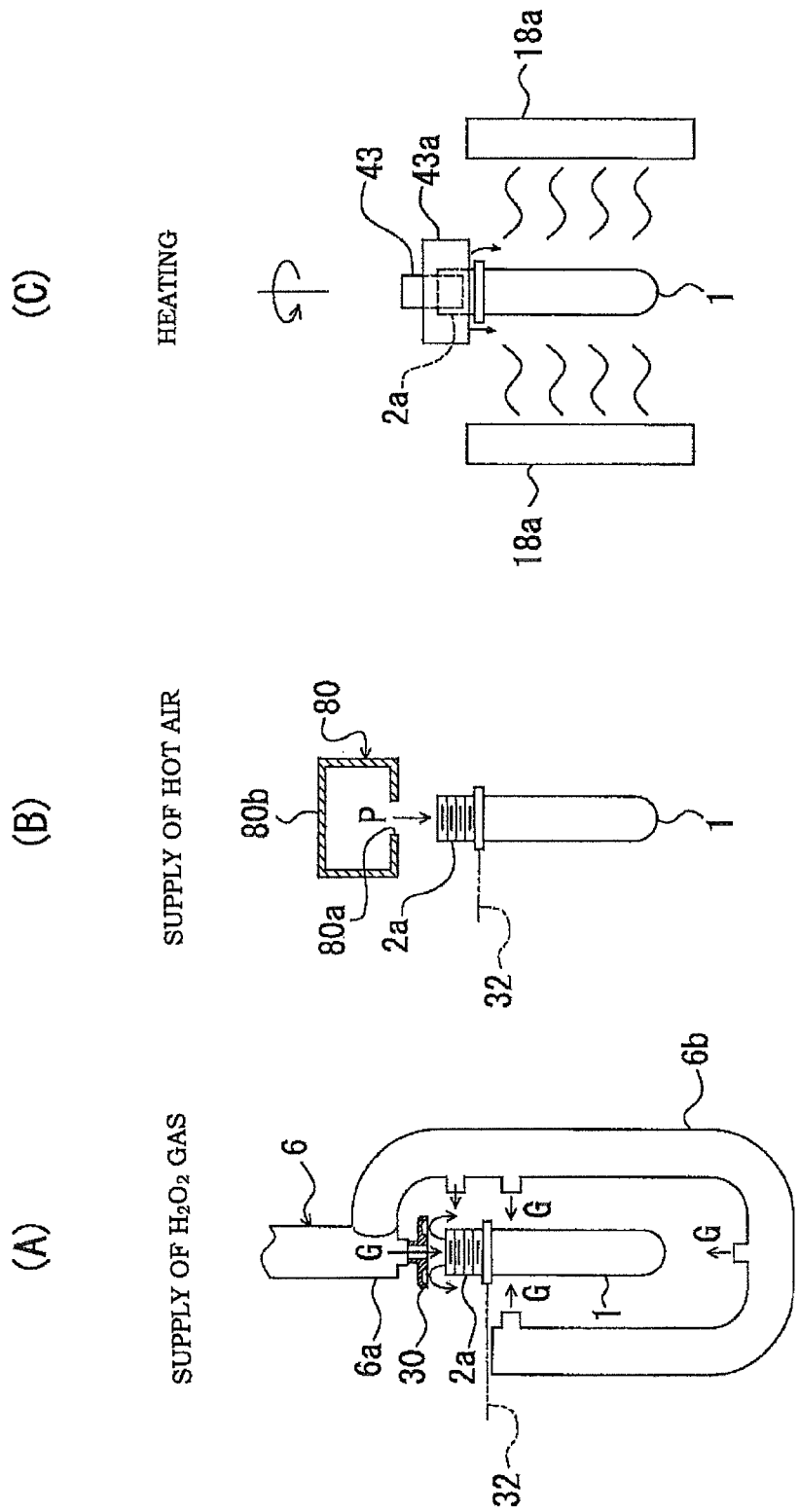
FIG. 11 represents a bottle sterilizing method according to a third embodiment of the present invention, in which (A), (B), and (C) show a hydrogen peroxide supply process to a preform, a hot-air supply process to the preform, and a heating process to the preform, respectively.

The bottle 2 is formed as an aseptic package through sterilizing process, molding process, drink filing process and sealing process as shown in FIG. 11 (A) to FIG. 14(K).

At first, the preforms 1 shown in FIG. 11(A) are continuously conveyed at a predetermined speed, and sterilizer gas G or mist, or their mixture is supplied to the preforms 1 now traveling.

The preform 1 has a structure similar to that of the preform 1 according to the first embodiment.

The sterilizer is also supplied in the same manner as in the first embodiment, and the gas G or mist of hydrogen peroxide or a mixture thereof as the sterilizer contacts and adheres to the inner and outer surfaces of the preform 1.

Part of the hydrogen peroxide on the surface of the preform 1 is adsorbed by the preform 1, and the remaining excess of the hydrogen peroxide remains on the surface of the preform 1.

Further, it may be possible to preliminarily heat the preform by, for example, blasting heated air to the preform 1 just before the blasting of the gas G to the preform 1 as shown in FIG. 11(A).

The preform 1 supplied with the hydrogen peroxide is also supplied with the hot air P by the air nozzle 80 as shown in FIG. 11(B). The hot air P can be supplied in the same manner as in the first embodiment.

By blasting the hot air P, the excess of the hydrogen peroxide remaining on the surface of the preform 1 is quickly removed from the surface of the preform 1.

As shown in FIG. 11(C), the sterilized preform 1 is heated by the infrared heater 18a and other heating means to a temperature suitable for the blow-molding treatment which will be performed thereafter. Such temperature is about 90° C. to 130° C. The mouth portion 2a of the preform 1 is made to prevent the heat of the infrared heater 18a from being transferred to the mouth portion 2a not to be deformed by the heat.

As also shown in FIG. 11(C), when the preform 1 is heated, the preform 1 is supported by the spindle 43.

Figure 16:
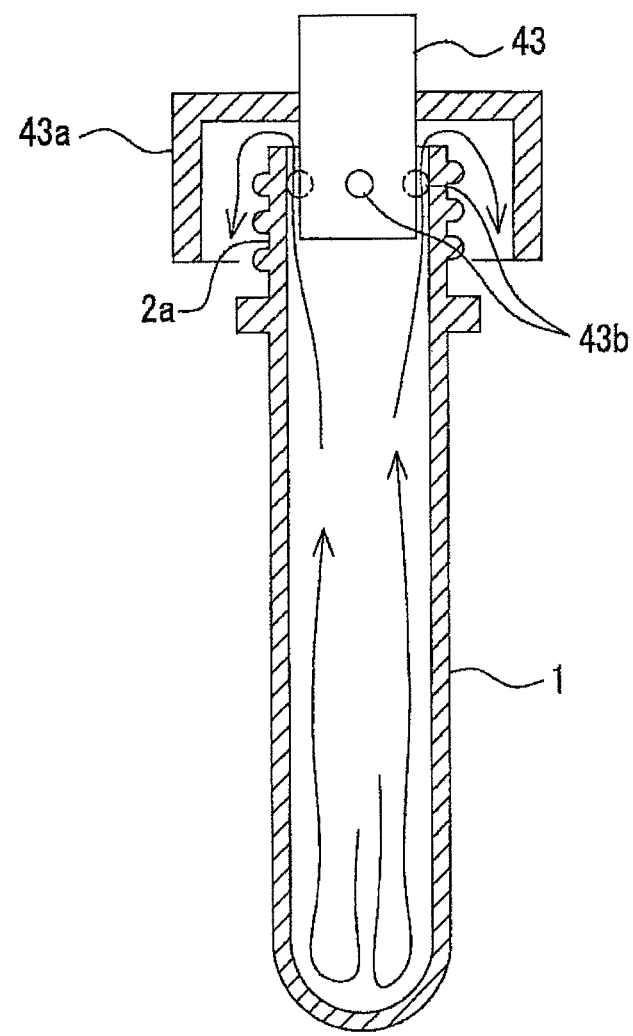
FIG. 16 is a vertical sectional view showing a nozzle for blasting the hot air into the preform in FIG. 11(C).

An umbrella-shaped member 43a is attached to an outer portion of the spindle 43 as occasion demands as shown in FIG. 16. And a plurality of elastic members 43b, each having a ball-like shape, are embedded.

When the lower portion of the spindle 43 is inserted into the mouth portion 2a of the preform 1, the preform 1 is supported to the spindle 43 by the elastic deformation of the elastic members 43b. In the case when the umbrella-shaped member 43a is provided, the mouth portion 2a of the preform 1 is covered by this umbrella-shaped member 43a.

As also shown in FIG. 16, when the umbrella-shaped member 43a is provided, a gap is formed to a portion between the inner surface of the mouth portion 2a of the preform 1 and the lower portion of the spindle 43, and a portion between the outer surface of the mouth portion 2a of the preform 1 and the umbrella-shaped member 43a. Because of the formation of such gap, the air inside the preform 1 heated by the heat from the infrared heater 18a changes to the hot air, which then flows outward of the preform 1 from the interior thereof through such gap while heating the mouth portion 2*a* of the preform 1.

It is necessary to pay attention so as not to deform the preform 1 by the heat at the state of the preform for the reason that the sealing performance of bottle 2 is kept at the time when the bottle 2 is sealed by the cap 3.

The hot air passing through the gap heats the mouth portion 2*a*, but attention should be paid so that the heating temperature is less than about 70° C., to prevent the deformation of the mouth portion 2*a*. According to such heating to the mouth portion 2*a*, very small amount of hydrogen peroxide remaining in the preform 1 is activated and the mouth portion 2*a* is hence properly sterilized.

When the preform 1 is heated as mentioned above, the preform 1 is conveyed in a state suspended at a positively standing attitude by the insertion of the spindle 43 into the mouth portion 2*a* thereof, preferably, while rotating together with the spindle 43 around the axis thereof. According to such operation, the preform 1 can be entirely, except the mouth portion 2*a*, heated evenly by the infrared heater 18*a* at a temperature about 90° C. to 130° C.

Further, the preform 1 may be conveyed in an inverted attitude.

By the heating of the preform 1 by the infrared heater 18*a*, the hydrogen peroxide adsorbed by the preform 1 is activated and sterilizes bacteria on the preform 1.

Figure 12:
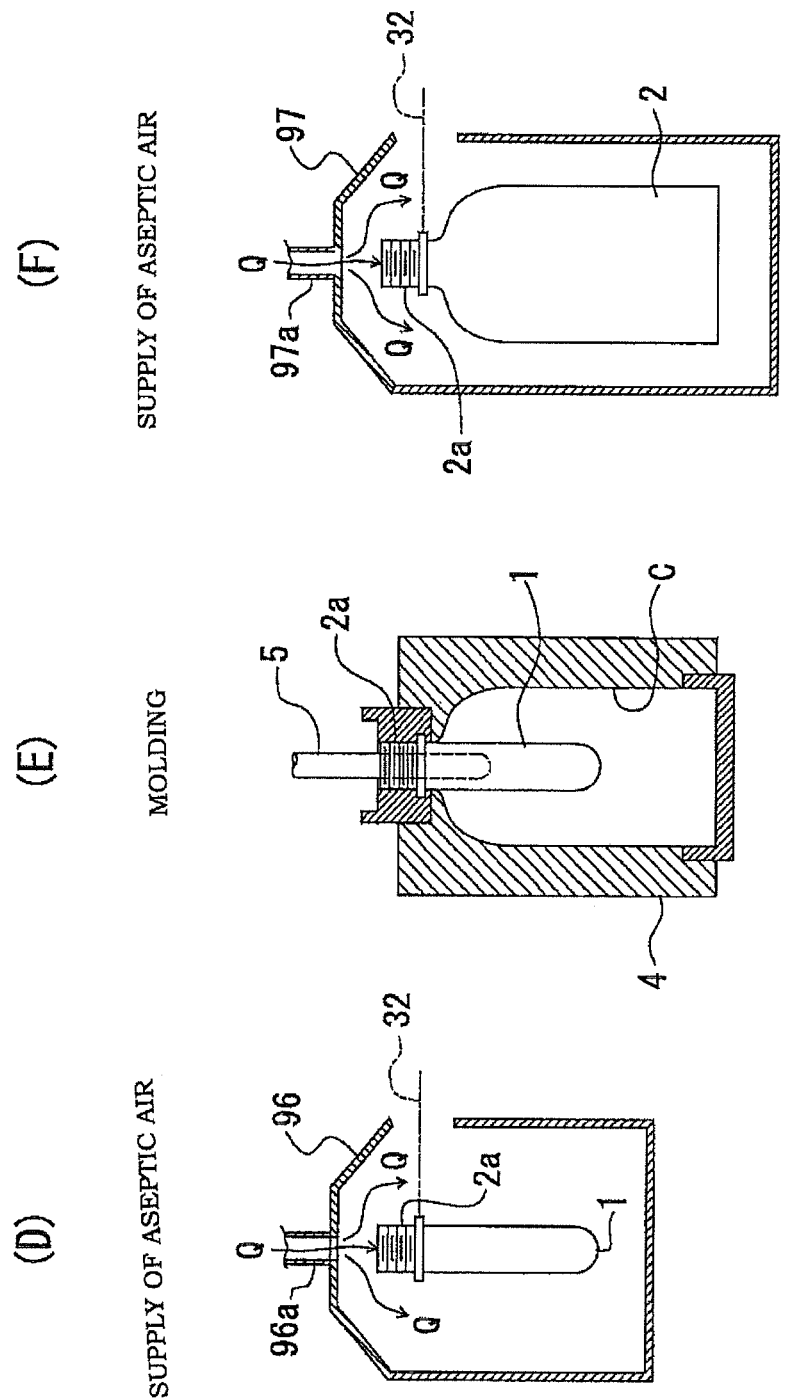
FIG. 12 includes (D), (E), and (F) representing an aseptic air blasting process to a preform, a bottle molding process to the preform and an aseptic air blasting process to the bottle, respectively.

The heated preform 1 is released from the spindle 43 as shown in FIG. 12(D), and conveyed to the mold 4 for being subjected to the blow-molding treatment while blasting an aseptic air Q from the mouth portion 2*a* as shown in FIG. 12(E). By such blasting of the aseptic air Q, the preform 1 can be moved into the mold 4 while keeping the aseptic condition.

Hot air may be used as such aseptic air Q. The preform 1 can be prevented from lowering in its temperature by the blasting of the hot air.

Further, as shown in FIG. 12(D), a cover 96 is disposed in form of a tunnel so as to surround the traveling path of the preform 1 at a portion at which the heated preform 1 is conveyed toward the mold 4. A top portion of the tunnel-shaped cover 96 covering the mouth portion 2*a* of the preform 1 from the upper side thereof is formed as a roof having an inclining surface. To such top portion, nozzles 96*a* through which the aseptic air Q is blasted toward the mouth portion 2*a* of the preform 1 are provided in form of line or slit. According to such structure, the aseptic air Q can be effectively supplied to the preform 1, and the preform 1 travels within the chamber 41*b* with the aseptic condition being maintained.

The preform 1 with the aseptic condition having been maintained by the blasting of the aseptic air Q is placed in the mold 4 as shown in FIG. 12(E).

The mold 4 is clamped (mold-clamped) while traveling at the same traveling speed as that of the preform 1, is subjected to the blow-molding treatment, and the mold 4 is thereafter opened.

As described above, the preform 1 is heated entirely, except the mouth portion 2*a* thereof, in the heating process shown in FIG. 11(C) to a temperature suitable for the molding the preform 1. Accordingly, as shown in FIG. 12(E), when the extension rod 5 is inserted into the preform 1 after being placed in the mold 4, the preform 1 is extended within the mold 4 in the longitudinal direction thereof.

Subsequently, when aseptic air for, for example, primary and secondary blow-molding treatments is blasted sequentially into the preform 1 from the blow nozzle, not shown, the preform 1 is expanded till the preform 1 is produced as a product bottle 2 in the cavity C of the mold 4.

After the bottle 2 is molded in the mold 4 in the manner mentioned above, the mold 4 is opened while being traveled, and the product bottle 2 is then taken out of the mold 4.

The bottle 2 after taken out of the mold 4 is conveyed till the hydrogen peroxide supply process shown in FIG. 13(G) starts while blasting the aseptic air Q from the mouth portion 2*a* side via nozzle 97*a*, as shown in FIG. 12(F). By the blasting of such aseptic air Q, the bottle 2 is conveyed directly below a hydrogen peroxide supply nozzle 93 so as not to be contaminated as possible as can by bacteria and the like fungus.

The aseptic air Q shown in FIG. 12(F) is preferably hot air. By blasting the hot air, since the temperature of the bottle 2 is prevented from lowering, the sterilizing effect by the hydrogen peroxide in the subsequent process can be expected to be improved.

Figure 13:
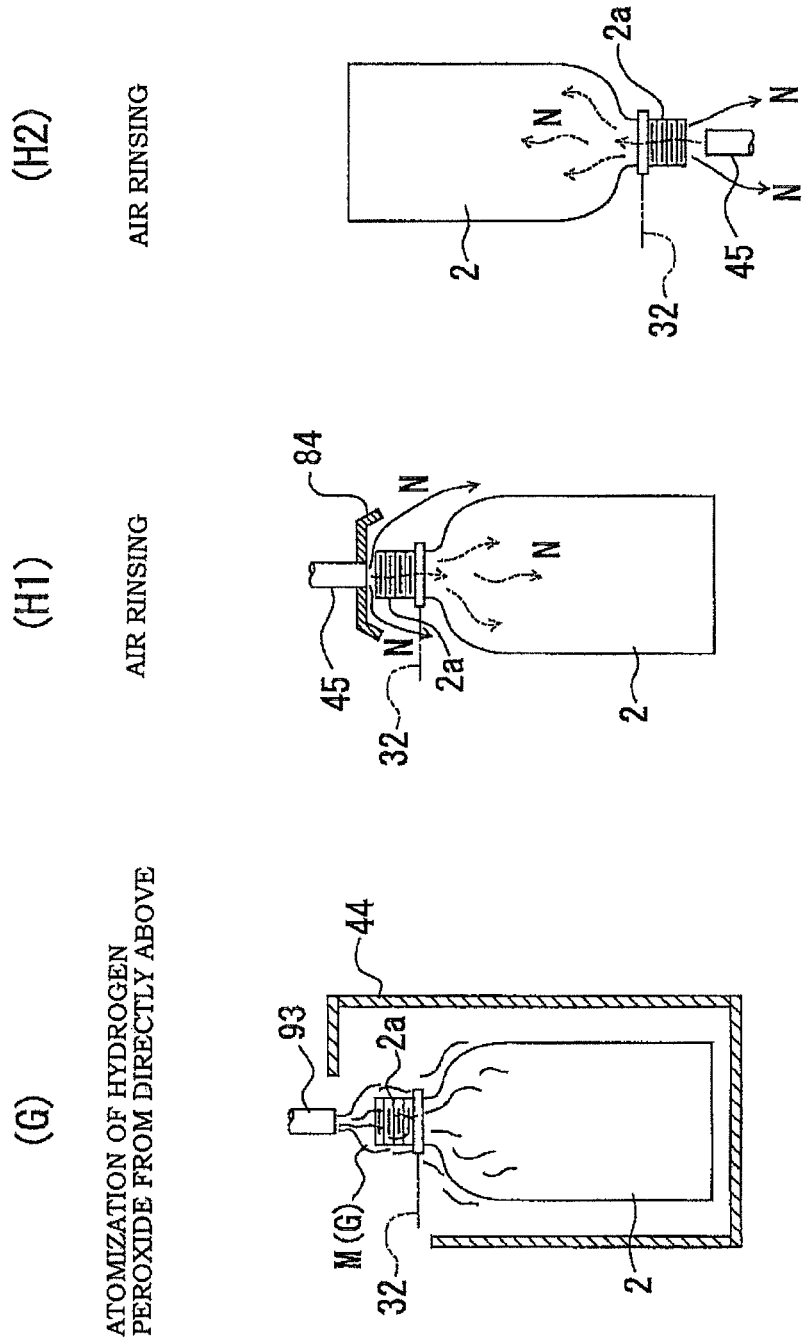
FIG. 13 includes (G), (H1), and (H2), in which (G) shows a hydrogen peroxide supply process to the bottle, and (H1) or (H2), which represent a hot water rinsing process, a content filling process, and a sealing process, respectively, after the hydrogen peroxide supply process.

Furthermore, as shown in FIG. 12(F), a cover 97 is disposed in form of a tunnel so as to surround the traveling path of the bottle 2 at a portion at which the bottle 2 is conveyed toward the hydrogen peroxide supply nozzle 93 (see FIG. 13 (G)). A top portion of the tunnel-shaped cover 97 covering the mouth portion 2*a* of the bottle 21 from the upper side thereof is formed as a roof having an inclining surface. To such top portion, nozzles 97*a* through which the aseptic air Q is blasted toward the mouth portion 2*a* of the bottle 2 or traveling path are provided in form of line or slit. According to such structure, the aseptic air Q can be effectively supplied to the preform 2, and the bottle 2 travels into the chambers 41*b* and 41*c* with the aseptic condition being maintained.

The bottle 2 blasted with the aseptic air Q is then sterilized by applying the hydrogen peroxide as sterilizer as shown in FIG. 13(G).

More specifically, the hydrogen peroxide mist M or gas G, or mixture thereof is blasted to the bottle 2 now being conveyed from the nozzle 93 for sterilization 93. The sterilizing nozzle 93 is arranged so as to face the mouth portion 2*a* of the bottle 2. The hydrogen peroxide mist M or gas G, or mixture thereof drops downward from the tip end of the sterilizing nozzle 93 into the bottle 2 through the mouth portion 2*a* thereof while contacting the inner surface of the bottle 2.

A tunnel 4 is provided to a portion on the traveling path of the bottle 2, and the hydrogen peroxide mist M or gas G, or mixture thereof discharged from the sterilizing nozzle 93 flows downward along the outer surface of the bottle 2 and stays inside the tunnel 44, so that the hydrogen peroxide mist M or gas G, or mixture thereof effectively adheres to the outer surface of the bottle 2.

The hydrogen peroxide mist M or gas G may be generated by the mist generator 7 shown, for example, in FIG. 4.

The sterilizing nozzle 93 may be located to a predetermined position on the way of the conveying path or moved synchronously with the bottle 2.

As shown in FIG. 13(G), the mist M or gas G, or mixture thereof contacts the inner and outer surfaces of the bottle 2, and at such instance, since the heat applied to the bottle 2 in the state of the preform 1 and in the state shown in FIG. 12(F) remains, the bottle 2 is maintained with the predetermined temperature, thus being effectively sterilized.

This predetermined temperature is preferably 40° C. to 80° C. in the case of the preform 1 being formed of PET, and more preferably, 50° C. to 75° C. In the case of less than 40° C., the sterilizing performance is extremely degraded, and on the other hand, in the case of more than 80° C., the bottle 2 may be contracted after the molding, thus being inconvenient.

After the blasting of the mist M or gas G, or mixture thereof, the bottle 2 is subjected to an air rinse treatment as shown in FIG. 13(H1). Such air rinsing is performed by blasting an aseptic air N from a nozzle 45 into the bottle 2, and the flow of such aseptic air N removes foreign substance, hydrogen peroxide or the like from the interior of the bottle 2. At that time, the bottle 2 keeps its positively standing attitude.

Preferably, an umbrella-shaped member 84 may be attached to the nozzle 45 as like as that shown in FIG. 9. The aseptic air N overflowing from the bottle 2 then flows toward the outer surface of the bottle 2 by the guidance of the inclination of the umbrella-shaped member 84, thereby rinsing the outer surface of the bottle 2.

Further, an air rinsing process shown in FIG. 13 (H2) may be adopted in place of the air rinsing process shown in FIG. 13(H1). In the air rinsing process shown in FIG. 13(H2), by blasting the aseptic air N into the bottle 2 through the mouth portion 2a thereof now directed downward, the foreign substance and the like can drop outward through the mouth portion 2a of the bottle 2. This air rinsing process shown in FIG. 13(H2) may be performed subsequently after the air rinsing process shown in FIG. 13(H1) by blasting the aseptic air N into the bottle 2. Furthermore, the umbrella-shaped member 84 may be attached to a nozzle 45 shown in FIG. 13(H2).

After the rinsing process, as occasion demands, the hydrogen peroxide adhering to the bottle 2 may be washed away and an aseptic air rinsing may be performed with aseptic water of normal temperature or hot water of 15° C. to 85° C. for removing the foreign substance and the like, as shown in FIG. 14(I). In such process, it may be preferred for one nozzle to be 5 L/min. to 15 L/min. for the cleaning rinsing time of 0.2 to 10 sec.

As described above, since the bottle 2 is sterilized furthermore by the hydrogen peroxide after the sterilization in the state of the preform 1, the using amount of the hydrogen peroxide can be reduced. Therefore, the rinsing step using hot water shown in FIG. 14(I), in which the hydrogen peroxide on the bottle 2 is washed away with hot water or the like after air rinsing, is not required. As occasion demands, however, the rinsing with aseptic water can be performed.

The hydrogen peroxide mist m or gas G used for the process shown in FIG. 13(G) will be explained hereunder.

In a case when the using amount of the hydrogen peroxide is converted into the hydrogen peroxide mist M for the sterilization of the bottle 2 only by the process shown in FIG. 13(G), the adhesion of the hydrogen peroxide of an amount of 50 μL/500 mL to 100 μL/500 mL thereof was needed for one bottle 2, whereas in a case when the preform 1 is sterilized by using the hydrogen peroxide of the using amount of 10 μL/500 mL to 50 μL/500 mL to be adhered to the bottle 2, it becomes possible to perform commercially available aseptic filling operation.

Furthermore, on the other hand, in a case when the using amount of the hydrogen peroxide is converted into the hydrogen peroxide gas G for the sterilization of the bottle 2 only by the process shown in FIG. 13(G), it was necessary to blast the hydrogen peroxide gas G of gas concentration of 5 mg/L to 10 mg/L to the bottle, whereas in a case of the present invention in which the preliminary sterilization due to the preliminary heating is performed to the preform 1, commercially available aseptic filling operation becomes possible by blasting the hydrogen peroxide gas of gas concentration of 1 mg/L to 5 mg/L.

After the above air rinsing process, the drink "a" fills the bottle 2 from the filling nozzle 10, as shown in FIG. 14(J), and as also shown in FIG. 14(K), the cap 3 as a lid is applied to the bottle 2 to be sealed, and the bottle 2 is produced as aseptic package.

Further, in this second embodiment, it may be possible to eliminate bottle sterilization processes corresponding to the processes shown in FIGS. 13 (G), (H1) and (H2), and the drink "a" fills the bottle 2 at a normal temperature under the aseptic condition after the sterilization process performed to the drink "a" itself.

Furthermore, it may be also possible to eliminate the bottle sterilization process mentioned above and to fill the bottle 2 with the drink "a" under a medium temperature of about 70° C. When the filling is performed at the medium temperature, existence of spore fungus within the drink "a" and the bottle 2 may be permitted, but mold, yeast or the like is sterilized by the heat possessed by the drink "a" itself, and the PET bottle 2 is not deformed. Accordingly, when the filling process is performed under the medium temperature, it is suitable for the drink "a" to be acidic drink or mineral water having a property for suppressing germination of the spore fungus.

Figure 14:
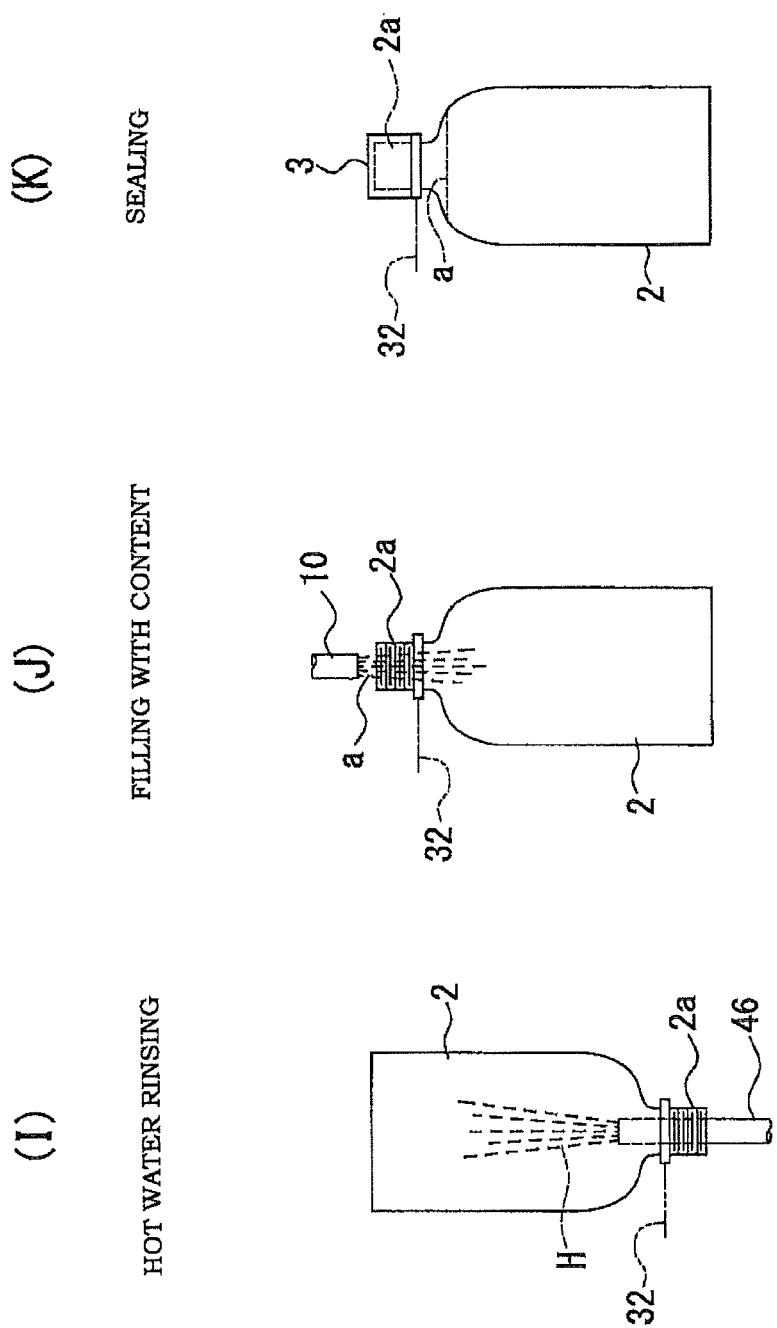
FIG. 14 includes (I), (J), and (K), which illustrate a hot water rinsing process, a content filling process and a sealing process, respectively, after the hydrogen peroxide supply process.

An aseptic filling apparatus for carrying out the method of sterilizing the bottle 2 as mentioned above has a structure or configuration shown in FIG. 14, for example.

Figure 15:
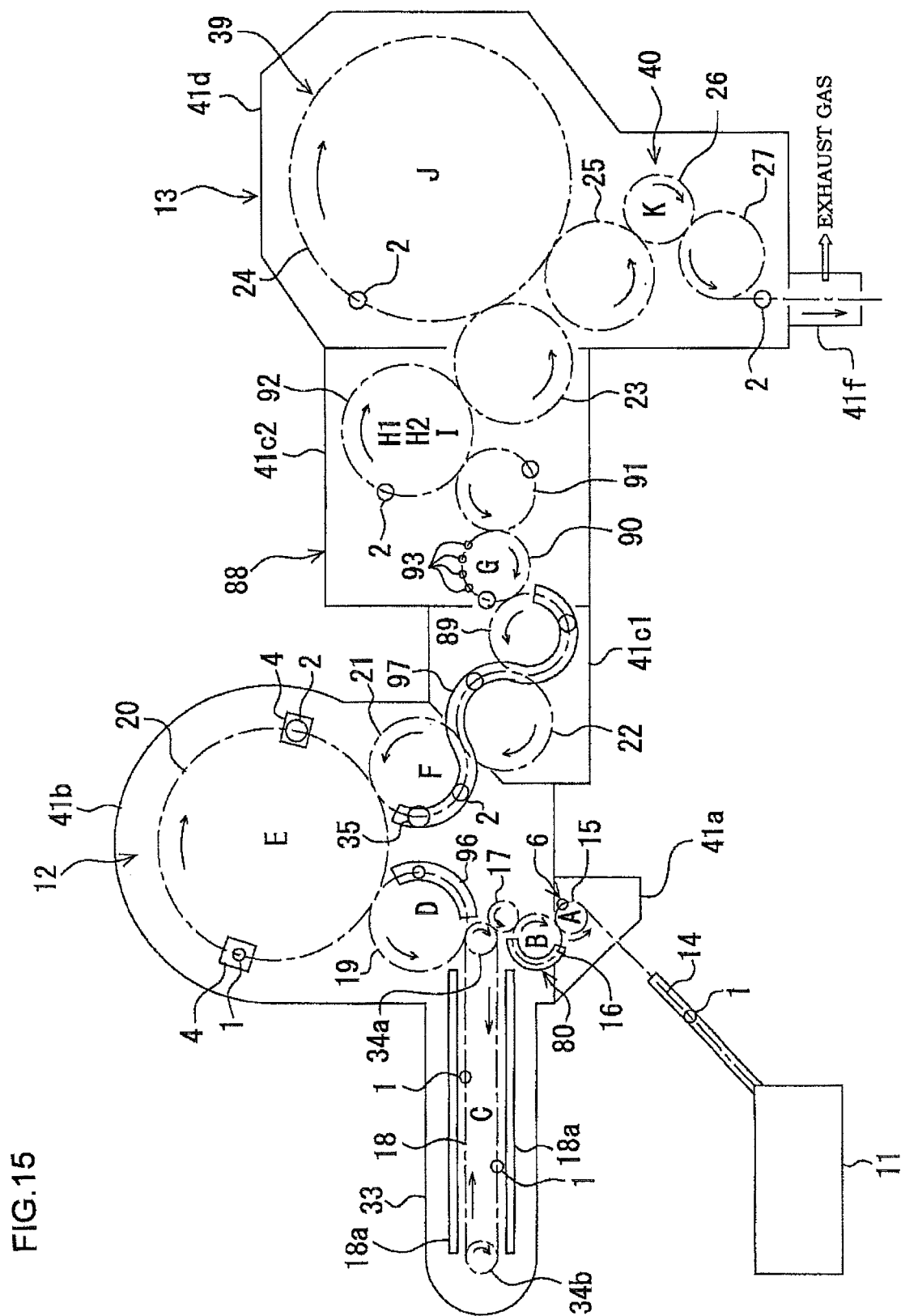
FIG. 15 is a plan view illustrating another example of an aseptic filling system incorporating the bottle sterilizing apparatus.

As shown in FIG. 15, the aseptic filling system is equipped with: the preform supplying machine 11 for supplying the preforms 1, each having a bottomed tubular shape and having the mouth portion 2a (see FIG. 11 (A)), subsequently at a predetermined interval; the blow-molding machine 12; the sterilizing machine 88 for sterilizing the molded bottles 2; and the filling machine 13 for filling the bottles 2 (see FIG. 12(F)) with the drink "a" and sealing the bottles 2 with the caps 3, respectively, (see FIG. 14(K)).

In this aseptic filling system, the portion between the blow-molding machine 12 to the filling machine 13 is covered by the chambers 41a, 41b, 41c1, 41c2, 41c3, 41d, 41e, and 41f.

The chamber 41a is located to the position corresponding to the portion at which the sterilizer is applied to the preform, the chamber 41b is located to the position corresponding to the portion at which the bottle 2 is molded, the chamber 41c1 is located to the position corresponding to the portion at which the bottle 2 is conveyed into the sterilizing machine 88, the chamber 41c2 is located to the position corresponding to the portion at which the sterilizer is applied to the bottle 2 and the bottle 2 is rinsed, and the chamber 41d is located to the position corresponding to the portion at which the bottle 2 is filed up with the drink "a" as a content and then sealed.

The portion between the chamber 41b to the chamber 41c1 is maintained as a clean room. In order to produce such clean room, positively pressurized aseptic air passing through the HEPA filter into the chambers 41b to 41c1 before the production of an aseptic package. According to such manner, the interiors of the chambers 41b to 41c1 are maintained to be clean, and it becomes possible to manufacture the bottle having high level of aseptic condition.

It may be possible to sterilize the interiors of the chambers 41b to 41c1 by the hydrogen peroxide gas G of less than 10 mg/L before the blasting the aseptic air having positive pressure thereinto. In addition, the portions to which the preform 1 and the bottle 2 contact may be irradiated with an UV lamp (for ultraviolet ray sterilization), or portions to which the mold 4, the extension rod 5, the gripper 32 and the like contact may be wiped up with chemical agent including ethanol or hydrogen peroxide of the amount of 1% by mass.

Between a portion from the preform supplying machine 11 to the filling machine 13, there are arranged a preform conveying means for conveying the preforms 1 on the first conveying path, a mold conveying means for conveying the molds 4 having cavities C, each in form of the product bottle 2, on the second conveying path connected to the first conveying path, and a bottle conveying means for conveying the bottles 2 molded by the molds 4 on the third conveying path connected to the second conveying path, while sterilizing and filling the bottles 2.

The first conveying path of the preform conveying means, the second conveying path of the mold conveying means and the third conveying path of the bottle conveying means are communicated with each other, and on the ways of these conveying paths, the grippers, not shown, for conveying the preforms 1 and the bottles 2 are located in the state of the bottle being held.

The preform conveying means is provided with a preform conveyer 14 on the way of the first conveying path for conveying the preforms 1 subsequently at a predetermined interval. The preform conveying means is further provided with a line of the wheels 15, 16 and 17 for receiving the preform 1 from the terminal end of the preform conveyer 14 and then conveying them, and the endless chain 18 for traveling the preforms 1 after the reception thereof.

Further, on the predetermined positions on the traveling path of the preform 1 in the wheel 15, there are also arranged the sterilizer gas generator 7 such as shown in FIG. 4 for generating the hydrogen peroxide gas G and the sterilizer supplying nozzle 6 such as shown in FIG. 11(A) for blasting the hydrogen peroxide gas G toward the preform 1.

Furthermore, on the predetermined position on the traveling path of the preform 1 in the wheel 16, there is also provided the air nozzle 80 (see FIG. 11(B)) fir activating the hydrogen peroxide adhering to the inner and outer surfaces of the preform 1 and discharging it out of the preform 1 by blasting the hot air P toward the preform 1.

As such air nozzle 8, the like nozzle shown in FIG. 5(A), (B) or FIG. 9 in connection with the first embodiment is usable.

As shown in FIG. 15, the wheels 15 and 16 are surrounded by the chamber 41*a*, which is coupled with the exhaust means composed of the filter 36 decomposing the sterilizer such as hydrogen peroxide in the air inside the chamber 41*a* and the blower 37 as like as the first embodiment as shown in FIG. 3. According to such arrangement, the flowing of the hydrogen peroxide into the adjacent blow-molding machine 12 can be prevented. Further, a heating furnace 33 for heating the preform 1 to a temperature suitable for molding the preform 1 is disposed to a portion, on the way of the first conveying path, from the wheel 17 contacting the wheel 16 to the wheel 19 contacting the second conveying path. This heating furnace 33 is also composed of as like as that in the first embodiment.

The preform 1 is evenly heated during the traveling within the heating furnace 33, and the preform 1 is heated entirely, except the mouth portion 2*a* thereof, to a temperature of 90° C. to 130° C. suitable for the blow-molding treatment. The mouth portion 2*a* is heated less than 70° C. so as not to damage the sealing performance when the cap 3 is applied.

The blow-molding machine 12 is arranged around the second conveying path. The blow-molding machine 12 has a structure as like as that of the first embodiment, which receives the preform 1 heated in the heating furnace 33 and molds the preform into the bottle 2.

Above the wheel 19 disposed between the first conveying path of the preform conveying means and the second conveying path of the mold conveying means, a cover 96 covering the mouth portion 2*a* of the preform 1 traveling around this wheel 19 is provided in a tunnel (FIG. 12(D)) so as to cover the mouth portion 2*a* from the upper side. Aseptic air Q is blasted into this cover 96 toward the mouth portion 2*a* of the preform 1. The aseptic air Q may be part of the aseptic air P supplied from the aseptic air supplying device shown in FIG. 5(B) in the first embodiment.

According to such arrangement as described above, the preform 1 is surrounded by the chamber 41*b* formed as a clean room and also covered by the cover 86 containing the aseptic air Q, and thus, the preform 1 is conveyed toward the blow-molding machine 12 with the high aseptic condition being maintained.

The mold 4 in the blow-molding machine 12 is opened at a position in contact to the wheel 21 as a starting end of the third conveying path, and the bottle 2 is received by the gripper, not shown, of the wheel 21.

The bottle 2 conveyed out of the blow-molding machine 12 to the wheel 21 is inspected by the inspection device 35 disposed as occasion demands to the periphery of the wheel 21 to inspect the presence of the defect in the molding process. As the inspection device, the like one as used in the first embodiment may be used.

In the inspection by the inspection device 35, the bottle 2 judged as defective is rejected by a rejection device, not shown, from the conveying path, and only the bottle 2 judged to be acceptable is conveyed to the wheel 22.

Above the traveling path of the bottle 2 in the wheels 21, 22 and 89 on the way of the third conveying path, a cover 97 covering the mouth portion 2*a* of the bottle 2 is provided in form of tunnel (FIG. 12(F)) so as to cover the mouth portion 2*a* thereof from the upper side. Aseptic air Q blasted into this cover 97 may be a part of the aseptic air P supplied from the aseptic air supplying device shown in FIG. 5(B) in the first embodiment.

A sterilizer supplying nozzle 93 (see FIG. 13(G)) and an aseptic air supplying nozzle 45 (see FIG. 13 (H1) or (H2)) are provided in the line of the wheels 90, 91, 92 and 23 continuous to the wheel 89 on the way of the third conveying path.

More specifically, a plurality of sterilizer supplying nozzles 93 (for example, four nozzles in FIG. 15) are located to predetermined positions on the way of the bottle traveling path around the wheel 90, and the tunnels 44(each shown in FIG. 13(G)) through which the bottle 2 passes is also located in correspondence with the sterilizer supplying nozzle 93. The hydrogen peroxide mist M or gas G, or mixture thereof blasted from the sterilizer supplying nozzle 93 enters the bottle 2 and adheres to the inner surface of the bottle 2 to thereby form a thin film, and also flows along the outer surface of the bottle 2, which then fills the interior of the tunnel 44 and adheres to the outer surface of the bottle 2 to thereby form a thin film thereon.

Further, one or a plurality of aseptic air supplying nozzles 45 are located to predetermined positions on the way of the bottle traveling path around the wheel 92. The aseptic air N blasted from the aseptic supplying nozzle 45 contacts the inner and outer surfaces of the bottle 2 and removes the film of the surplus hydrogen peroxide adhering to the surface of the bottle 2. When the hot air is used as such aseptic air N, the hydrogen peroxide adhering to the inner and outer surfaces of the bottle 2 is activated, thereby enhancing the sterilizing effect.

The sterilizer supplying nozzles 93 and the aseptic air supplying nozzles 44 are located around the wheel 90 and 92, respectively, at the same pitch as that of the bottles 2, and the hydrogen peroxide gas G and the aseptic air N are blasted into the bottles 2 while being turned synchronously therewith.

The filler 39 and the capper 40 are located to positions on the way from the wheel 24, to which the wheel 23 is contacted, to the wheel 27 in the third conveying path.

More specifically, the filler 39 is constituted by a number of filling nozzles 10 (see FIG. 14(J)) located around the wheel 24 each for filling the bottle 2 with the drink "a", and the capper 40 is for applying the cap 3 (see FIG. 14(K)) disposed around the wheel 26 to the bottle 2 filled up with the drink "a".

The filler 39 and the capper 40 are ones identical to those of the first embodiment.

The periphery of the wheel 15 is surrounded by the chamber 41a on the way of the first to third conveying paths. The peripheral portion from the wheel 16 to the wheel 21 is surrounded by the chamber 41b. The peripheral portion from the wheel 22 and the wheel 89 is surrounded by the chamber 41c1. The peripheral portion from the wheel 90 to the wheel 23 is surrounded by the chamber 41c2. The peripheral portion from the wheel 24 to the wheel 27 is surrounded by the chamber 41d.

Aseptic air cleaned by the HEPA filter, not shown, is always supplied into the chamber 41b. Accordingly, the chamber 41b is constituted as a clean room, thus preventing bacteria or like fungus from entering into the chamber 41b.

The interiors of these chambers 41a, 41b, 41c1, 41c2, 41d, 41e and 41f are sterilized by, for example, the COP (cleaning outside of place) treatment and the SOP (sterilizing outside of place) treatment, and thereafter, the sterilizer and the cleaner gas or mist in the chambers 41a, 41b, 41c2, 41d, 41e and 41f are exhausted from the chambers 41a, 41b, 41c2, 41d, 41e and 41f outside thereof by the exhausting means such as shown in FIG. 3, respectively. Then, by supplying aseptic air sterilized by a scrubber, filter and the like means into these chambers 41a, 41b, 41c2, 41d, and 41f, the aseptic condition within the chambers 41a, 41b, 41c2, 41d, and 41f can be maintained. Further, although the COP and the SOP treatments are necessarily performed for the chambers 41d, 41e and 41f, it is not always necessary to perform such treatments for the chambers 41a, 41b, and 41c2.

Furthermore, the chambers 41c1 functions as a atmosphere shut-off chamber for shutting off the atmosphere between the chamber 41b and the chamber 41d, thereby preventing the cleaner gas or like generated by the COP and SOP treatments and the sterilizer mist or like generated in the chamber 41c2 from flowing into the chamber 41b of the blow-molding machine 12 via the chamber 41c1.

Hereunder, the function or operation of the drink filling system will be explained with reference to FIGS. 11 to 16.

At first, the preform 1 is conveyed by the line of the wheels 15, 16 and 17 toward the heating furnace 33.

When the preform 1 is traveled around the wheel 15 before the entering into the heating furnace 33, the sterilizer gas G or mist M, or the mixture thereof is supplied to the preform 1 through the sterilizer supplying nozzle 6.

Subsequently, when the preform 1 to which the hydrogen peroxide adheres is traveled around the wheel 16, the hot air P is blasted from the air nozzle 80 to the preform 1. The hydrogen peroxide adhering to the preform 1 is activated by the heat of the hot air P to thereby sterilize the bacteria and the like fungus. In addition, the surplus hydrogen peroxide adhering to the surface of the preform 1 is removed by such heat of the hot air P.

Foreign substance in the preform 1 can be blasted out of the interior of the preform 1 by blasting the hot air P by means of the air nozzle 81 shown in FIG. 7, and the blasted foreign substance may be recovered by a suction tube 82. On the other hand, by arranging the air nozzle 81 and the preform 1 in the inverted attitude as shown in FIG. 8 with respect to the attitude shown in FIG. 7, the foreign substance in the preform 1 may be removed our of the preform 1.

Thereafter, the preform 1 is received by the spindle 43 on the endless chain 18 (see FIG. 11(C)), and then transferred to the heating furnace 33.

The preform 1 is then heated by the infrared heater 18a within the heating furnace 33, and the preform 1 is entirely heated, except the mouth portion 2a thereof, to the temperature suitable for the blow-molding treatment.

The preform 1 heated in the heating furnace 33 to the temperature suitable for the blow-molding treatment is blasted with the aseptic air Q while passing under the cover 96 during the traveling around the wheel 19. According to such blasting of the aseptic air Q, the preform 1 is conveyed to the blow-molding machine 12 while the aseptic condition being maintained. In the case where the aseptic air Q is hot air, the preform 1 can arrive at the blow-molding machine 12 with the temperature suitable for the blow-molding treatment being maintained.

When the preform 1 passes around the outer periphery of the wheel 20, the preform 1 is held by the mold 4 as shown in FIG. 12(E), and is blasted with the highly pressurized aseptic air so that the preform 1 is expanded into the product bottle 2 within the cavity C of the mold 4.

The product bottle 2 is taken out of the mold 4 by the gripper of the wheel 21 after opening the mold 4, and thereafter, is subjected to the inspection by the inspection device 35 whether the molding defective is present or not.

The defective bottle 2 is removed from the conveying line by the rejecting device, not shown, and only the acceptable (good) bottle 2 is transferred to the wheel 22 and then conveyed to the sterilizing machine 88.

Further, in the time when the bottle 2 is traveled from the wheel 21 to the wheel 89, the aseptic air Q is blasted to the bottle 2 while passing under the cover 97. Accordingly, the bottle 2 is conveyed to the sterilizing machine 88 with the aseptic condition being maintained. In the case where the aseptic air Q is hot air, the preform 1 can arrive at the sterilizing machine 88 while maintaining the temperature suitable for the sterilization.

The bottle 2 is sterilized by blasting the hydrogen peroxide mist M or gas G, or the mixture thereof, as shown in FIG. 13(G)), while traveling around the wheel 90 within the sterilizing machine 88, and subsequently, the bottle 2 is air-rinsed by blasting the aseptic air N as shown in FIG. 13(H1) or (H2) while traveling around the wheel 92.

Thereafter, the bottle 2 enters the interior of the filing machine 13.

The bottle 2 in the filling machine 13 is filled up with the preliminarily sterilized drink "a" through the filling nozzle 10 of the filler 39 as shown in FIG. 14(J). The bottle 2 filled up with the drink "a" is applied with the cap 3 by the capper 40 to be sealed (see FIG. 14(K)), and then discharged out of the aseptic filling system through an outlet of the chamber 41d.

Fourth Embodiment

Figure 17:
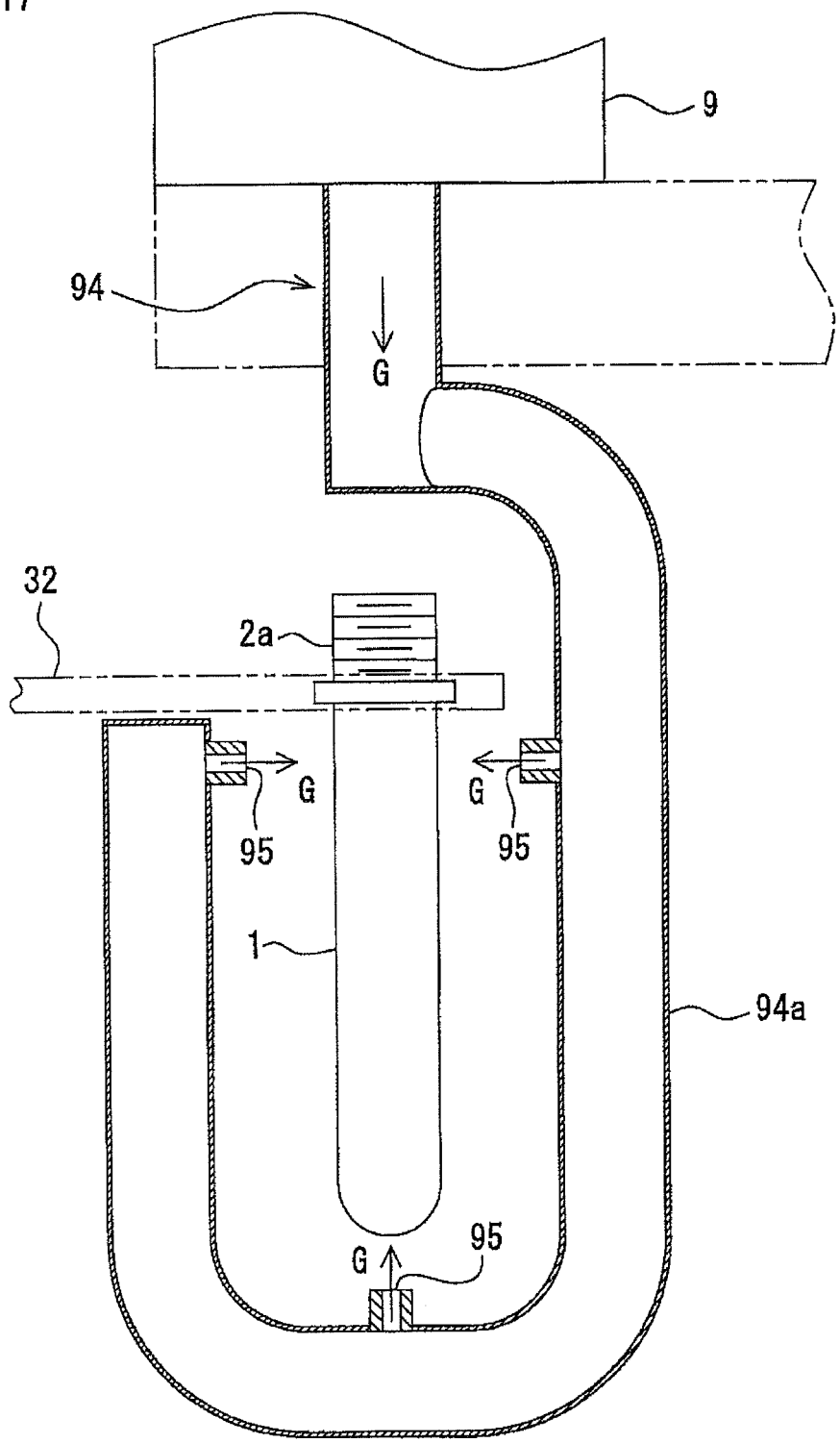
FIG. 17 is a vertical sectional view of a nozzle used in place of the sterilizer supply nozzle shown in FIG. 6.

In this fourth embodiment, a sterilizer supplying nozzle 94 shown in FIG. 17 is used in place of the sterilizer supplying nozzle 6 shown in FIG. 11(A) in the third embodiment in the process of supplying the sterilizer to the preform 1.

As shown in FIG. 17, the sterilizer supplying nozzle 94 is equipped with a pipe line 94a extending in U-shape along the preform 1, and a discharge port 95 is formed to the pipe line 94a so as to face the outer surface of the preform 1. A plurality of such discharge ports 95 are located at several portions so as to face the lower portions below the mouth portion 2a of the preform 1 to thereby prevent the hydrogen peroxide as the sterilizer from entering into the preform 1.

The hydrogen peroxide gas G generated by a generator like the sterilizer gas generator 7 used in the second embodiment is blasted toward the outer surface of the preform from the discharge port 95 of the sterilizer supplying nozzle 94, and such gas G or mist, or the mixture thereof is blasted to the outer surface of the preform, except the mouth portion 2a thereof. The hydrogen peroxide gas G or like does not enter the preform 1 and adheres to the outer surface of the preform 1. As a result, bacteria or like fungus existing on the outer surface of the preform 1 can be sterilized.

Further, the hydrogen peroxide existing in the pipe line 94a of the sterilizer supplying nozzle 94 may be prevented from being condensed as dew by supplying hot air as the aseptic air.

Furthermore, such condensation as dew of the hydrogen peroxide in the pipe line 94a may be also prevented by winding a ribbon heater around the pipe line 94a.

In the fourth embodiment, the preform 1 having been subjected to the sterilizer supplying process by the sterilizer as shown in FIG. 11(A) is then subjected to the respective processes shown in FIGS. 11(B) and (C), and thereafter, subjected to the hot water rinsing process shown in FIG. 14(I). Although the excessive hydrogen peroxide is removed from the outer surface of the preform 1 in the step shown in FIG. 11(B), this step may be omitted as required. During such processes, the processes shown in FIG. 13(G), (H1) and (H2) are eliminated.

As shown in FIG. 14(I), in the hot water rinsing process, the bottle 2 has an inverted attitude with the mouth portion 2a directed downward, and the aseptic hot water H is supplied into the bottle 2 by a hot water supplying nozzle 46 inserted into the bottle 2. The hot water H contacts entirely the inner surface of the bottle 2, and thereafter, is discharged out of the bottle 2 through the mouth portion 2a thereof. The temperature of the hot water H is maintained to a temperature range at which the bottle 2 is not deformed, for example, about 70° C. to 85° C. A flow rate per one nozzle is 5 L/min. to 15 L/min., and it is desirable to set a cleaning rinsing time to be about 0.2 to 10 sec.

The bacteria and the like fungus in the bottle 2 can be sterilized by the hot water rinsing process mentioned above. The bacteria to be sterilized is, for example, fungus, yeast and the like, and spore forming fungus remains as it is.

Accordingly, the method of this third embodiment is preferably applicable to the manufacture of drink not requiring sterilization of spore germination fungus such as acidic drink, carbonated drink, mineral water or the like other than sub-acidity drink.

After the hot water rising treatment, the drink "a" fills the bottle 2 as shown in FIG. 14(J), and the cap 3 is applied to the bottle 2 to thereby seal the same as shown in FIG. 14(K).

Further, in this fourth embodiment, it may be possible to eliminate the hot water rinsing treatment to the bottle 2 (FIG. 14(I)), and to sterilize the interior of the bottle 2 by filling the bottle 2 with the drink "a" having a middle temperature of about 70° C. In the drink filling treatment at the middle temperature, the spore fungus permits to remain within the drink "a" and the bottle 2, but mold, yeast and the like fungus are sterilized by the heat of the drink "a", and the PET bottle 2 can be prevented from deforming. Accordingly, the drink filling operation at the middle temperature is suitable for a drink "a" such as acidic drink and mineral water having property of suppressing germination of the spore fungus.

Fifth Embodiment

According to the fifth embodiment, an aseptic package provided with a bottle 2 and a cap 3 such as shown in FIG. 14(K) can be manufactured.

Figure 18:
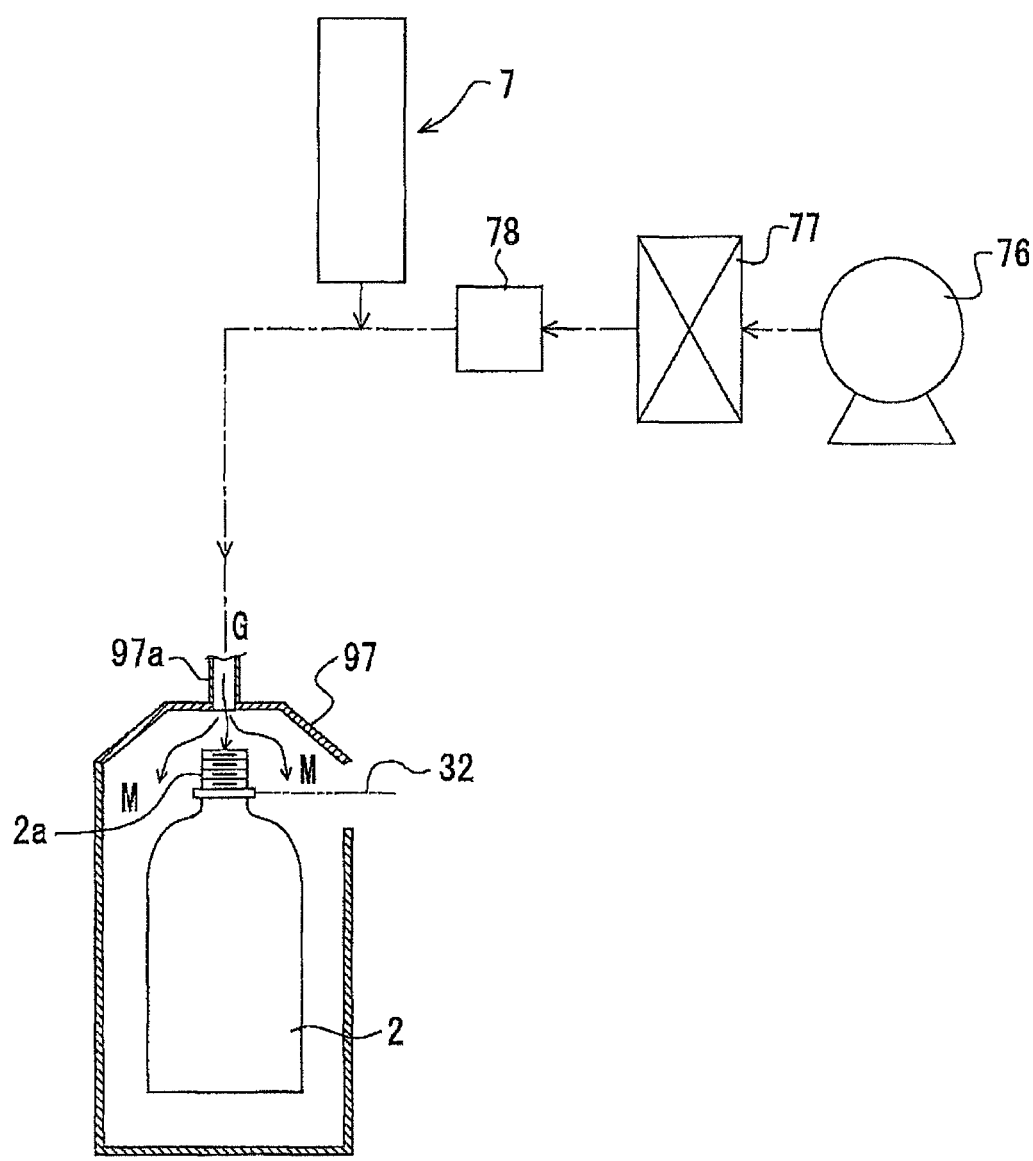
FIG. 18 is a view illustrating a modified example of the aseptic air supply process.

The bottle 2 is formed as an aseptic package via the sterilizing process, molding process, drink filing process and sealing process as shown in FIG. 11 (A), (B), (C), FIG. 12(D), (E), FIG. 18, and FIG. 14(J), (K).

At first, the preforms 1 shown in FIG. 11(A) are continuously conveyed at a predetermined speed, and sterilizer gas G or mist, or their mixture is supplied to the preforms 1 now traveling.

Further, the preform 1 sown in FIG. 11(A) may be preliminarily heated by blasting the hot air to the preform 1 immediately before the blasting of the gas G to the preform 1.

The hot air P is supplied by the air nozzle 80 to the preform 1 to which the hydrogen peroxide has been supplied, as shown in FIG. 11(B).

The hydrogen peroxide adhering to the surface of the preform 1 is activated by the heat of the hot air P, thereby sterilizing bacteria or like fungus inside the preform 1. In addition, by blasting the hot air P, the hydrogen peroxide adhering to the surface of the preform 1 can be promptly removed therefrom.

As shown in FIG. 11(C), the sterilized preform 1 is then heated by the infrared heater 18a or other heating means to a temperature suitable for the subsequent blow-molding treatment.

The heated preform 1 is, as shown in FIG. 12(D), released from the spindle 43, blasted with the aseptic air Q from the mouth portion side, and then, conveyed toward the mold 4 shown in FIG. 12(E) for the blow-molding treatment. According to such blasting of the aseptic air Q, the preform 1 is supplied to the mold 4 with the aseptic condition being maintained.

The preform 1 conveyed with the aseptic condition being maintained by the blasting of the aseptic air Q is conveyed into the mold 4 as shown in FIG. 12(E), into which the preform 1 is molded to a bottle 2.

The bottle 2 taken out of the mold 4 is conveyed while being blasted with the hydrogen peroxide mist M from the mouth portion side as shown in FIG. 18 till the bottle 2 reaches the portion for the drink filling operation shown in FIG. 14(J).

Further, in FIG. 18, the same reference numerals are added to the structural portions as that shown in FIGS. 4 and 5(B).

The hydrogen peroxide mist M is produced by a device shown in FIG. 18. That is, the bottle 2 is sterilized by passing the air flow by the blower 76 through the HEPA filter 77, heated by the heater 8, and fed to the outlet of the sterilizer gas generator 7 as heated wind (heated air). The hydrogen peroxide gas G generated by the sterilizer gas generator 7 is taken into the heated wind, then conveyed into the cover 97 through the nozzle 97a, and thereafter changes as the hydrogen peroxide mist M.

The hydrogen peroxide mist M flows down to the bottle 2 now traveling inside the cover 97 from the upper side of the mouth portion 2a and adheres to the outer surface of the bottle 2.

Furthermore, since the mist M fills the interior of the tunnel-shaped cover 97, the mist M adheres evenly to the inner and outer surfaces of bottle 2 in a state of an extremely thin film. The concentration of the hydrogen peroxide mist M is thinly diluted, and the inner and outer surfaces of the bottle 2 can be hence easily sterilized by the hydrogen peroxide component and the heat of the air-flow.

The air flow conveying the mist M provides positive pressure within the cover 97 to thereby block the invasion of the bacteria or like into the cover 97 and hence prevent the contamination of the bottle 2. Even if the bacteria invades into the cover 97, it is sterilized by the hydrogen peroxide.

After the bottle 2 passes through the cover 97, the drink "a" fills the bottle 2 through the filling nozzle 10 as shown in FIG. 14(J), and as shown in FIG. 14(K), the bottle 2 is applied with the cap 3 as a lid to thereby produce the bottle 2 as aseptic package.

Figure 19:
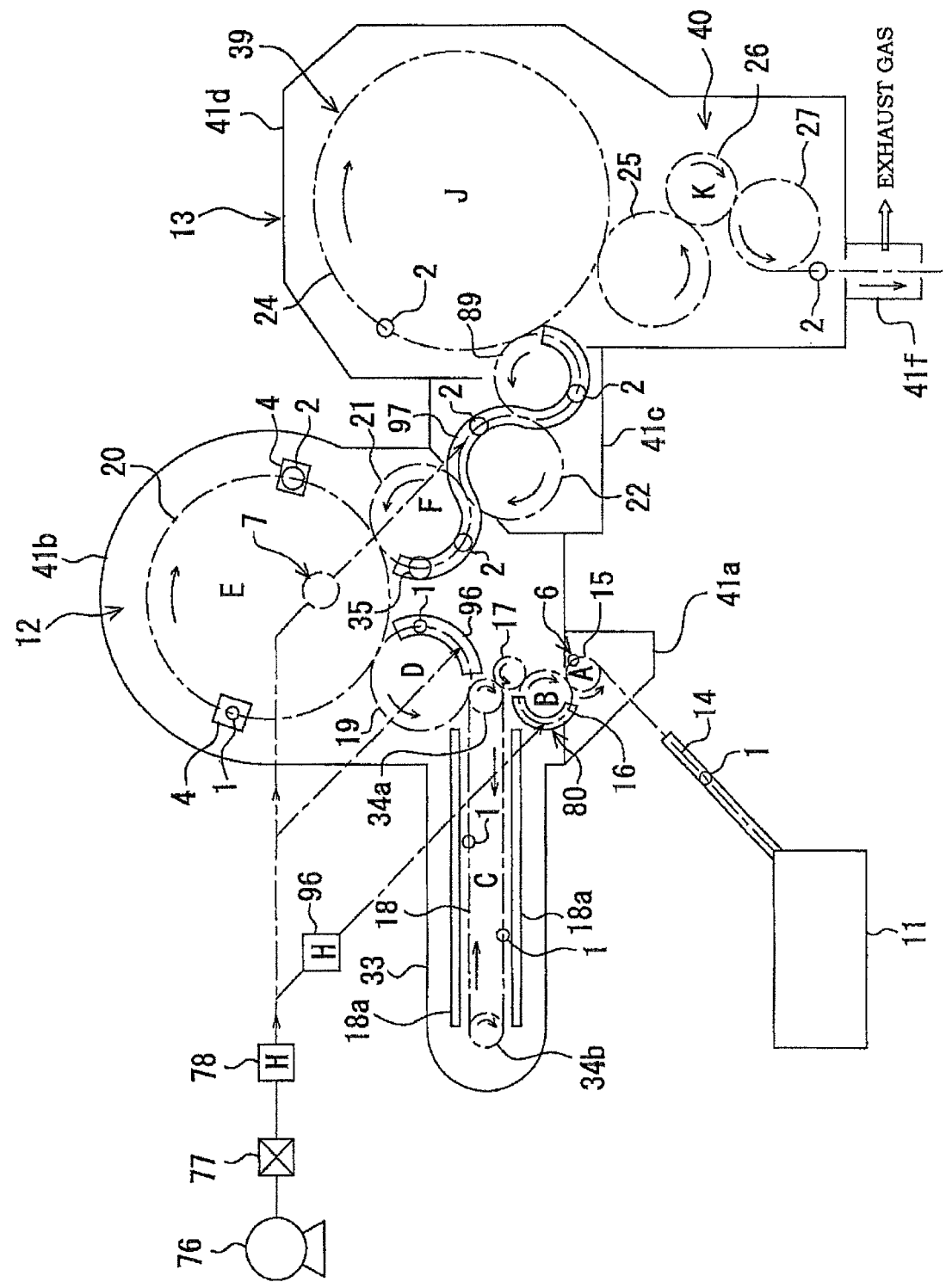
FIG. 19 is a plan view showing an aseptic filling system incorporating the process shown in FIG. 18.

The aseptic filling system for carrying out the method of sterilizing the bottle 2 has a configuration or structure shown in FIG. 19, for example.

As shown in FIG. 19, the aseptic filling system is provided with the preform supplying machine 11 for subsequently supplying the preforms 1, each having a bottomed-tubular shape and a mouth portion 2a, at a predetermined interval (see FIG. 11(A)), the blow-molding machine 12, and the filling machine 13 which fills the molded bottle 2 (see FIG. 18) with the drink "a" (see FIG. 14(J)) and applies the cap 3 to the bottle 2 to seal the same (see FIG. 14(K)).

In the aseptic filling system, the portion extending from the blow-molding machine 12 to the filling machine 13 is surrounded by the chambers 41a, 41b, 41c, 41d, 41e and 41f.

The chamber 41a corresponds to the portion at which the sterilizer is supplied to the preform 1, the chamber 41b corresponds to the portion at which the bottle 2 is molded, the chamber 41c corresponds to the portion at which the bottle 2 is transferred to the content filling position, the chamber 41d corresponds to the portion at which the drink "a" fills the bottle 2, and the chamber 41e corresponds to the portion at which the bottle 2 is applied with the cap 3 to seal the bottle 2.

An outlet conveyer, not shown, is provided to an outlet portion of the bottle 2 in the chamber 41e, and this outlet conveyer is surrounded by the chamber 41f.

The portion extending from the chamber 41b to the chamber 41c is maintained as a clean room, and in order to form such clean room, the positively pressurized aseptic air suitable for the HEPA filter is supplied into the chambers 41b and 41c before the manufacture of the aseptic package. According to such arrangement, the interiors of the chambers 41b and 41c are maintained in the clean state, and it becomes possible to produce the bottle having high aseptic (i.e. sterilized) level.

Before the blasting of the positively pressurized aseptic air, the interior of the chambers 41b and 41c may be sterilized by the hydrogen peroxide gas of less than 10 mg/L. Furthermore, a portion to which the preform 1 or bottle 2 is contacted may be irradiated with an UV lamp (ultraviolet ray sterilization), or a portion to which the members or components such as mold 4, the extension rod 5, and the gripper 32 may be wiped by a chemical agent including ethanol or hydrogen peroxide of 1%.

A preform conveying means, a mold conveying means and a bottle conveying means are located between the preform supplying machine 11 and the filling machine 13, in which the mold conveying means is for conveying the preforms 1 on the first conveying path, the mold conveying means is for conveying the mold 4 having a cavity "C" having a shape corresponding a final product of the bottle 2 (see FIG. 2(D)) on the second conveying path connected to the first conveying path, and the bottle conveying means is for conveying the bottle 2 molded by the mold 4 on the third conveying path connected to the second conveying path while sterilizing the bottle 2 and being filled with the drink "a".

The first conveying path for the preform conveying means, the second conveying path for the mold conveying means and the third conveying path for the bottle conveying means are communicated with each other, and grippers and like members, not shown, for holding and conveying the preforms 1 and the bottles 2 are provided on these conveying paths.

The structure or configuration between the first conveying path and the second conveying path is similar to that of the second embodiment, and the detailed explanation will be omitted herein.

The cover 97 (see FIG. 18) is provided in form of tunnel above the bottle traveling path in the wheels 21, 22 and 89 on the way of the third conveying path so as to cover the mouth portion 2a of the bottle 2 from the upper side thereof.

An aseptic air supplying device such as shown in FIG. 18 is connected to a portion corresponding to the wheel 22 disposed substantially the inner central portion of the cover 97.

This aseptic air supplying device has a conduit extending from the blower 76 to the cover 97, and the HEPA filter 77 and the heater 78 are provided on the way of this conduit toward the downstream side. A sterilizer gas generator like the sterilizer gas generator 7 shown in FIG. 4 is provided between the heater 78 and the cover 97 on the way of the conduit.

According to the structure mentioned above, the air flow form the blower 76 is sterilized by the HEPA filter 77 and then heated by the heater 78, and the heated air formed as aseptic hot air flows inside the conduit, and flows into the cover 97 from the nozzle 97a while being added with small amount of the hydrogen peroxide gas G frequently. The hydrogen peroxide gas G flows into the cover 97 from the nozzle 97a, and the bottle 2 travels in the cover 97 filled up with the hydrogen peroxide gas G.

The concentration of the hydrogen peroxide gas G is set to be less than 5 mg/L, and preferably, less than 3 mg/L. In a case when the hydrogen peroxide gas concentration is more than 5 mg/L, the hydrogen peroxide gas remains inside the bottle 2, and the gas concentration may exceed 0.5 ppm as the reference of FDA. However, if the bottle 2 has large volume, remaining amount of the hydrogen gas intends to become less, and in such case, the hydrogen peroxide gas concentration may be set to be higher than 5 mg/L.

Further, as shown in FIG. 19, the aseptic hot air from the aseptic air supplying device described above is heated further by another heater 96, and thereafter, supplied to the air nozzle 80, and also supplied into the cover 86 for the preform 1.

On the way of the third conveying path, the filler 39 and the capper 40 are disposed to portions from the wheel 24 continued to the wheel 89 to the wheel 27.

More specifically, the filler 39 is composed of a number of the filling nozzles 10 (see FIG. 14(J)) for filling the bottle 2 with the drink "a" around the wheel 24, and the capper 40 for sealing the bottle 2 with the cap 3 (see FIG. 14(K)) is provided around the wheel 26.

Next, the operation and function of the aseptic filling system will be explained with reference to FIGS. 18 and 19.

At first, the preforms 1 are conveyed toward the heating furnace 33 by the preform conveyer 14 and the lines of the wheels 15, 16, 17.

At the time when the preforms 1 travel around the wheel 15 before the entering of the preforms 1 into the heating furnace 33, the hydrogen peroxide gas G or mist, or their mixture is supplied toward the preforms 1 from the sterilizer supplying nozzles 6.

Sequentially, the hot air P is blasted from the air nozzle 80 to the preform 1 at the time when the preform adhered with the hydrogen peroxide travels around the wheel 16. The hydrogen peroxide adhering to the preform 1 is activated by the heat of the hot air P, and bacteria and like fungus adhering to the preform 1 can be sterilized. Moreover, the surplus hydrogen peroxide is removed by the blasting of the hot air P from the surface of the preform 1.

The blasting of the hot air P is performed by the air nozzle 81 shown in FIG. 7. The foreign substance existing in the preform 1 is blasted outward, and the thus blasted foreign substance may be recovered by the suction tube 82. Further, as shown in FIG. 8, the preform 1 and the air nozzle 82 may be inverted in attitude compared with those shown in FIG. 7 to thereby remove the foreign substance existing in the preform 1 outward.

Thereafter, the preform 1 is received by the spindle 43 (see FIG. 11 (C)) above the endless chain 18, and then conveyed into the heating furnace 33.

The preform 1 in the heating furnace 33 is heated by the infrared heater 18*a* to thereby evenly heat the entire of the preform, except the mouth portion 2*a*, to a temperature range suitable for the blow molding treatment.

When the preform 1 heated in the heating furnace 33 travels around the outer periphery of the wheel 19, the preform 1 is blasted with the aseptic air Q while passing through the interior of the cover 86 (see FIG. 12(D)). According to this operation, the preform 1 is conveyed to the blow-molding machine 12 while the aseptic condition being maintained. In the case of the aseptic air Q being the hot air, the preform reaches to the blow-molding machine 12 while the temperature suitable for the molding treatment being maintained.

When the preform 1 travels around the outer periphery of the wheel 20, it is held by the mold 4 as shown in FIG. 12(E), and the preform 1 is expanded by blasting the highly pressurized aseptic air in the cavity C of the mold 4.

The thus molded bottle 2 is taken out of the mold 4 after opening the mold 4 by the gripper of the wheel 21, and the bottle 2 is then inspected by the inspection device 35 as to whether it is defective product or not.

Thereafter, the defective bottle 2 is rejected outward from the traveling line of the bottles by a rejecting device, not shown, and only a acceptable (non-defective) bottle 2 is transferred to the wheels 22 and 89 and conveyed on the downstream side.

When the bottle 2 travels from the wheel 21 to the wheel 89, the aseptic hot air Q added with fine amount of the hydrogen peroxide is blasted while passing through the cover 97. By the heat contained in the hot air Q and the hydrogen peroxide, bacteria and like fungus which may invade into the chamber 41*b* can be sterilized, and the bottle 2 is thereby conveyed on the downstream side while maintaining the aseptic condition. The hydrogen peroxide is decomposed when or after the bottle 2 exits from the cover 97, and the bottle 2 without any remaining hydrogen peroxide is conveyed into the filling machine 13.

The bottle 2 passing out of the cover 97 travels toward the filling machine 13, in which the bottle 2 is filled with the drink "a" preliminarily sterilized by the filling nozzle 10 of the filler 39 as shown in FIG. 14(J). The bottle 2 filled up with the drink "a" is applied with the cap 3 by the capper 40 to be sealed (see FIG. 14(K)), and discharged outside the aseptic filling system through the outlet port of the chamber 41*d*.

In this fourth embodiment, the like reference numerals are added to components and members corresponding to those of the other embodiments, and the detailed descriptions thereof will be omitted herein.

Sixth Embodiment

According to the sixth embodiment, an aseptic package provided with a bottle 2 and a cap 3 such as shown in FIG. 14(K) can be manufactured.

Figure 20:
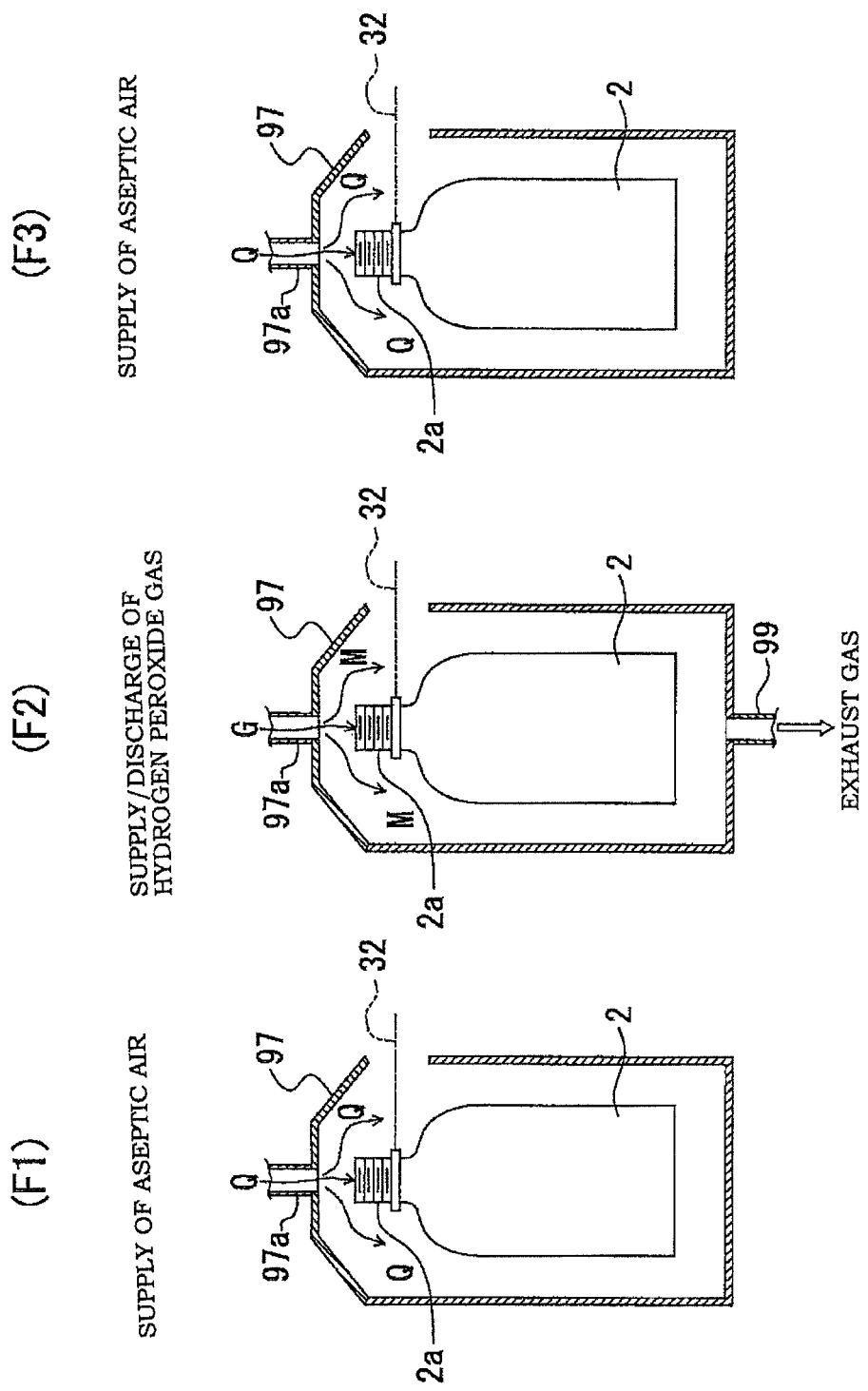
FIG. 20 is a view illustrating another modified example of the aseptic air supply process.

The bottle 2 is formed as an aseptic package through sterilizing process, molding process, sterilizing process, drink filing process and sealing process as shown in FIG. 11 (A), (B), (C), FIG. 12(D), (E), FIG. 20, and FIG. 14(J), (K).

At first, the preforms 1 shown in FIG. 11(A) are continuously conveyed at a predetermined speed, and sterilizer gas G or mist, or their mixture is supplied to the preforms 1 now traveling.

Further, the preform 1 sown in FIG. 11(A) may be preliminarily heated by blasting the hot air to the preform 1 immediately before the blasting of the gas G to the preform 1.

The hot air P is supplied by the air nozzle 80 to the preform 1 to which the hydrogen peroxide has been supplied, as shown in FIG. 11(B).

The hydrogen peroxide adhering to the surface of the preform 1 is activated by the heat of the blasted hot air P, thereby sterilizing bacteria or like fungus inside the preform 1. In addition, by blasting the hot air P, the hydrogen peroxide adhering to the surface of the preform 1 can be promptly removed therefrom.

As shown in FIG. 11(C), the sterilized preform 1 is then heated by the infrared heater 18*a* or other heating means to a temperature suitable for the subsequent blow-molding treatment.

The heated preform 1 is, as shown in FIG. 12(D), released from the spindle 43, blasted with the aseptic air Q from the mouth portion side, and then conveyed toward the mold 4 shown in FIG. 12(E) for the blow-molding treatment. According to such blasting of the aseptic air Q, the preform 1 is supplied to the mold 4 with the aseptic condition being maintained.

The preform 1 conveyed with the aseptic condition being maintained by the blasting of the aseptic air Q is conveyed into the mold 4 as shown in FIG. 12(E), into which the preform 1 is molded to a bottle 2.

The bottle 2 taken out of the mold 4 is conveyed in the cover 97 till the bottle 2 reaches to a portion for the drink filling process shown in FIG. 14(J). In a front stage of the cover 97, as shown in FIG. 20(F1), the aseptic hot air Q is blasted, in a middle stage of the cover 97, as shown in FIG.

20(F2), the bottle 2 is conveyed while the hydrogen peroxide gas G or mist M, or their mixture being blasted on the mouth portion side, and in a subsequent last stage of the cover 97, as shown in FIG. 20(F3), the bottle 2 is conveyed while being blasted with the aseptic hot air Q. In the case of the remaining hydrogen peroxide concentration in the bottle 2 is less than 0.5 ppm as the reference of the FDA, the normal temperature of hot air Q may be usable.

The bottle 2 is heated by blasting the aseptic hot air Q in the front stage of the cover 97 while the aseptic condition being maintained. According to this process, the bottle 2 travels in the middle stage of the cover 97 while maintaining the predetermined temperature, and then, the hydrogen peroxide flowing into the middle stage of the cover 97 is activated to thereby sterilize bacteria or like which may invade from the molding-machine side. When the bottle 2 passes the subsequent last stage of the cover 97, the surplus hydrogen peroxide adhering to the inner and outer surfaces of the bottle 2 is rinsed by the aseptic hot air Q and removed from the surfaces of the bottle 2. Thus, the bottle 2 is conveyed toward the next filling machine 23 while the aseptic condition being maintained.

When the bottle 2 passes the cover 97 and enters the filling machine 13, the drink "a" fills the bottle 2 from the filling nozzle 10 as shown in FIG. 14(J), and then, as shown in FIG. 14(K), the bottle 2 is applied and sealed with the cap 3 to thereby form the bottle 2 as aseptic package.

Figure 21:
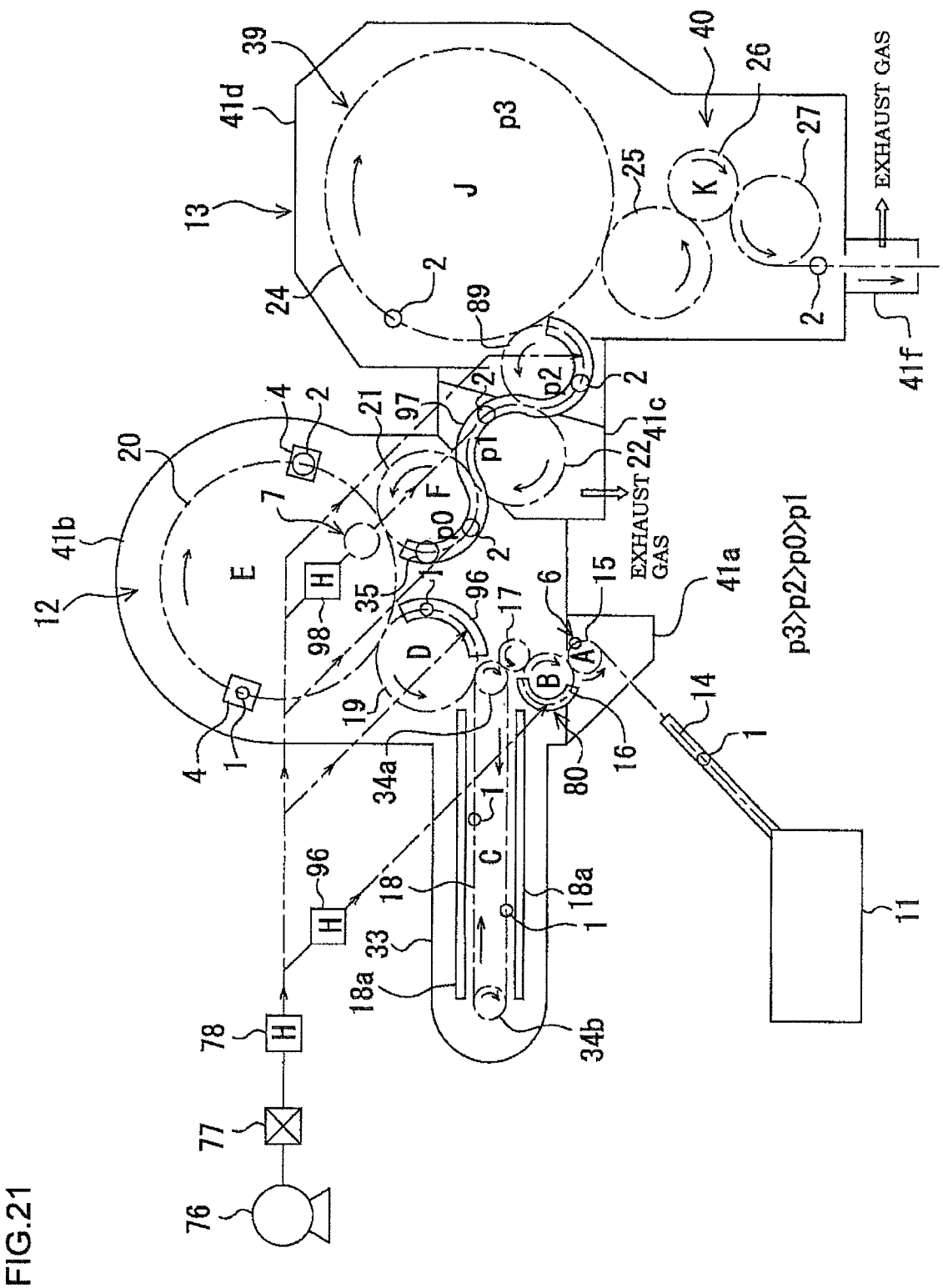
FIG. 21 is a plan view illustrating the aseptic filling system incorporating the process shown in FIG. 20.

The aseptic filling system for carrying out the bottle sterilizing method has a configuration or structure shown in FIG. 21, for example.

As shown in FIG. 21, the aseptic filling system is equipped with the preform supplying machine 11 for supplying the preforms 1, each having a bottomed tubular shape and having the mouth portion 2a (see FIG. 11 (A)), subsequently at a predetermined interval, the blow-molding machine 12, the sterilizing machine 88 for sterilizing the molded bottles 2 (see FIG. 20), and the filling machine 13 for filling the bottles 2 with the drink "a" (see FIG. 14(J)) and sealing the bottles 2 with the caps 3, respectively, (see FIG. 14(K)).

In this aseptic filling system, the portion between the blow-molding machine 12 and the filling machine 13 is covered by the chambers 41a, 41b, 41c, 41d, 41e, and 41f.

The chamber 41a is located to the position corresponding to the portion at which the sterilizer is applied to the preform, the chamber 41b is located to the position corresponding to the portion at which the bottle 2 is molded, the chamber 41c is located to the position corresponding to the portion at which the bottle 2 is conveyed to the content filling position, and the chamber 41d is located to the position corresponding to the portion at which the bottle 2 is filed up with the drink "a" as a content and then sealed.

The portion between the chamber 41b and the chamber 41c is maintained as a clean room. In order to produce such clean room, positively pressurized aseptic air passing through the HEPA filter, not shown, into the chambers 41b to 41c1 before the production of an aseptic package. According to such manner, the interiors of the chambers 41b to 41c are maintained to be clean, and it becomes possible to manufacture the bottle 2 having high level of aseptic condition.

It may be possible to sterilize the interiors of the chambers 41b to 41c by the hydrogen peroxide gas G of less than 10 mg/L before blasting the aseptic positive pressure thereinto. In addition, the portions to which the preform 1 and the bottle 2 are contacted may be irradiated with an UV lamp (for ultraviolet ray sterilization), or portions to which the mold 4, the extension rod 5, the gripper 32 and the like are contacted may be wiped up with chemical agent including ethanol or hydrogen peroxide of the amount of 1%.

Between a portion from the preform supplying machine 11 to the filling machine 13, there are arranged a preform conveying means for conveying the preforms 1 on the first conveying path, a mold conveying means for conveying the molds 4 having cavities C (see FIG. 12(E)), each in form of the product bottle 2, on the second conveying path connected to the first conveying path, and a bottle conveying means for conveying the bottles 2 molded by the molds 4 on the third conveying path connected to the second conveying path, while sterilizing and filling the bottles 2.

The first conveying path of the preform conveying means, the second conveying path of the mold conveying means and the third conveying path of the bottle conveying means are communicated with each other, and on the ways of these conveying paths, the grippers, not shown, for conveying the preforms 1 and the bottles 2 are disposed in the state of the bottle being held.

The structure between the first conveying path and the second conveying path is the same as that of the second embodiment, and the details thereof will be omitted herein.

On the way of the third conveying path, the cover 97 (see FIG. 20) covering the bottle 2 from the upper side of the mouth portion 2a thereof is provided in form of a tunnel.

An aseptic air supplying device such as shown in FIG. 18 is connected to a portion corresponding to the wheel 22 disposed substantially in the inner central portion of the cover 97.

This aseptic air supplying device has a conduit extending from the blower 76 to the cover 97, and the HEPA filter 77 and the heater 78 are provided on the way of this conduit toward the downstream side. A sterilizer gas generator like the sterilizer gas generator 7 shown in FIG. 4 is provided between the heater 78 and the cover 97 on the way of the conduit.

According to the structure mentioned above, the air flow from the blower 76 is sterilized by the HEPA filter 77 and then heated by the heater 78, and the heated air formed as aseptic hot air flows inside the conduit, and flows into the cover 97 from the nozzle 97a while being added with a small amount of the hydrogen peroxide gas G frequently. The hydrogen peroxide gas G flows into the cover 97 through the nozzle 97a, and the bottle 2 travels in the cover 97 filled up with the hydrogen peroxide gas G.

The concentration of the hydrogen peroxide gas G is set to be less than 5 mg/L, and preferably, less than 3 mg/L. In a case when the hydrogen peroxide gas concentration is more than 5 mg/L, the hydrogen peroxide gas remains inside the bottle 2, and the gas concentration may exceed 0.5 ppm according to FDA standards. However, if the bottle 2 has large volume, remaining amount of the hydrogen gas tends to become less, and in such case, the hydrogen peroxide gas concentration may be set to be higher than 5 mg/L.

Further, as shown in FIG. 21, the aseptic hot air from the aseptic air supply device described above is further heated by another heater 96, and thereafter, supplied to the air nozzle 80 as well as within the cover 86 for the preform 1.

On the way of the third conveying path, the filler 39 and the capper 40 are located to portions between the wheel 24 subsequent to the wheel 89 and the wheel 27.

More specifically, a number of filling nozzles 10 (see FIG. 14(J) for filling the bottles 2 with the drink "a" are arranged around the wheel 26 to thereby constitute the filler 39, and around the wheel 26, the capper 40 for applying the cap 3 (see FIG. 14(K)) to each of the bottles 2 to seal it.

The surrounding of the wheel 15 is surrounded by the chamber 41a on the way of the first to third conveying paths. The peripheral portion from the wheel 16 to the wheel 21 is surrounded by the chamber 41b. The peripheral portion of the wheel 22 and the wheel 89 is surrounded by the chamber 41c. The peripheral portion from the wheel 24 to the wheel 27 is surrounded by the chamber 41d.

The aseptic air cleaned by the HEPA filter, not shown, is always supplied into the chamber 41b, and as a result, the chamber 41b is constituted as a clean room into which the invasion of bacteria is blocked.

The interiors of these chambers 41a to 41f are subjected to the sterilization treatment by performing the COP and SOP treatments, and thereafter, the gas or mist of the sterilizer and the cleaner is discharged from these chambers by the exhaust means such as shown in FIG. 3 which are provided integrally with or respectively to these chambers 41a to 41f. Then, the aseptic air cleaned by the filter or like, not shown, is supplied into these respective chambers 41a to 41f to thereby maintain the aseptic condition in the respective chambers 41a and 41d.

Further, the chambers 41a, 41b and 41c are not portions to be splashed with product liquid such as drink. Since the interiors of the chambers 41a and 41c are exposed to a chemical agent during the manufacture, these chambers are free from the COP and SOP treatments with no risk of contamination by bacteria or like fungus.

Herein, supposing that a pressure inside the chamber 41d by the blasting of the aseptic air is p3, and pressures in the inner central portion, the upstream side portion, and the downstream side portion of the cover 97 are respectively p1, p0, and p2, the pressures are adjusted to be p3>p2>p0>p1. More specifically, with reference to the atmospheric pressure, these pressures are set such that the pressure p3 is 30 to 100 Pa, the pressure p2 is 10 to 30 Pa, the pressure p0 is 0 to 10 Pa, and the pressure p1 is −30 to 0 Pa. According to such relationship between these pressures, the hydrogen peroxide supplied to the inner central portion of the cover 97 is blocked to flow into the upstream side portion and the downstream side portion thereof. Moreover, the air flow from the chamber 41c side and the air containing the hydrogen peroxide can be perfectly blocked from entering the chamber 41d in which the filling machine 39 is located.

Next, the operation and function of the aseptic filling system will be explained with reference to FIGS. 20 and 21.

At first, the preforms 1 are conveyed toward the heating furnace 33 by the preform conveyer 14 and the lines of the wheels 15, 16, 17.

At the time when the preforms 1 travel around the wheel 15, the hydrogen peroxide gas G or mist, or their mixture is supplied toward the preforms 1 from the sterilizer supplying nozzles 6 before the entering of the preforms 1 into the heating furnace 33.

Sequentially, the hot air P is blasted from the air nozzle 80 to the preform 1 at the time when the preform adhered with the hydrogen peroxide travels around the wheel 16. The hydrogen peroxide adhering to the preform 1 is activated by the heat of the hot air P, and bacteria and like fungus adhering to the preform 1 can be sterilized. Moreover, the surplus hydrogen peroxide is removed by the blasting of the hot air P from the surface of the preform 1.

The blasting of the hot air P is performed by the air nozzle 81 shown in FIG. 7. The foreign substance existing in the preform 1 is blasted outward and the thus blasted foreign substance may be recovered by the suction tube 82. Further, as shown in FIG. 8, the preform 1 and the air nozzle 82 may be inverted in attitude compared with those shown in FIG. 7 to thereby remove the foreign substance existing in the preform 1 outward.

Thereafter, the preform 1 is received by the spindle 43 (see FIG. 11 (C)) above the endless chain 18, and then conveyed into the heating furnace 33.

The preform 1 in the heating furnace 33 is heated by the infrared heater 18a to thereby evenly heat the entire of the preform, except the mouth portion 2a, to a temperature range suitable for the blow molding treatment.

When the preform 1 heated in the heating furnace 33 travels around the outer periphery of the wheel 19, the preform 1 is blasted with the aseptic air Q while passing through the interior of the cover 86. In the case of the aseptic air Q being the hot air, the preform reaches to the blow-molding machine 12 while the temperature suitable for the molding treatment being maintained.

When the preform 1 travels around the outer periphery of the wheel 20, it is held by the mold 4 as shown in FIG. 12(E), and the preform 1 is expanded by blasting the highly pressurized aseptic air in the cavity C of the mold 4.

The thus molded bottle 2 is taken out of the mold 4 after opening the mold 4 by the gripper of the wheel 21, and the bottle 2 is then inspected by the inspection device 35 as to whether it is defective product or not.

Thereafter, the defective bottle 2 is rejected outward from the traveling line of the bottles by a rejecting device, not shown, and only a acceptable (non-defective) bottle 2 is transferred to the wheel 22 and then to the sterilizing machine 88.

When the bottle 2 travels from the wheel 21 to the wheel 89, the aseptic hot air Q is blasted while passing through the cover 97 on the upstream side as shown in FIG. 20(F1). According to such blasting, the bottle 2 is traveled toward the inner central portion while maintaining the aseptic condition. In the central portion, the bottle 2 is blasted with the hydrogen peroxide mist M. As a result, the hydrogen peroxide films are formed to the inner and outer surfaces of the bottle 2. Furthermore, in the downstream side portion, the aseptic air Q is blasted so as to activate the hydrogen peroxide adhering to the inner and outer surfaces of the bottle 2, and the surplus hydrogen peroxide is decomposed and then removed.

The bottle 2 travels toward the filling machine 13, in which the bottle 2 is filled with the drink "a" preliminarily sterilized by the filling nozzle 10 of the filler 39 as shown in FIG. 14(J). The bottle 2 filled up with the drink "a" is applied with the cap 3 by the capper 40 to be sealed (see FIG. 14(K)), and discharged outside the aseptic filling system through the outlet port of the chamber 41d.

In this fifth embodiment, the like reference numerals are added to components and members corresponding to those of the other embodiments, and the detailed descriptions thereof will be omitted herein.

Seventh Embodiment

According to the seventh embodiment, an aseptic package provided with a bottle 2 applied with a cap 3 as like as the sixth embodiment shown in FIG. 14(K) can be manufactured.

Furthermore, the bottle 2 is manufactured as an aseptic package through sterilizing process, molding process, sterilizing process, drink filing process and sealing process as shown in FIG. 11 (A), (B), (C), FIG. 12(D), (E), FIG. 20 (F1), (F2), (F3) and FIG. 14(J), (K) as in the case of the sixth embodiment.

Figure 22:
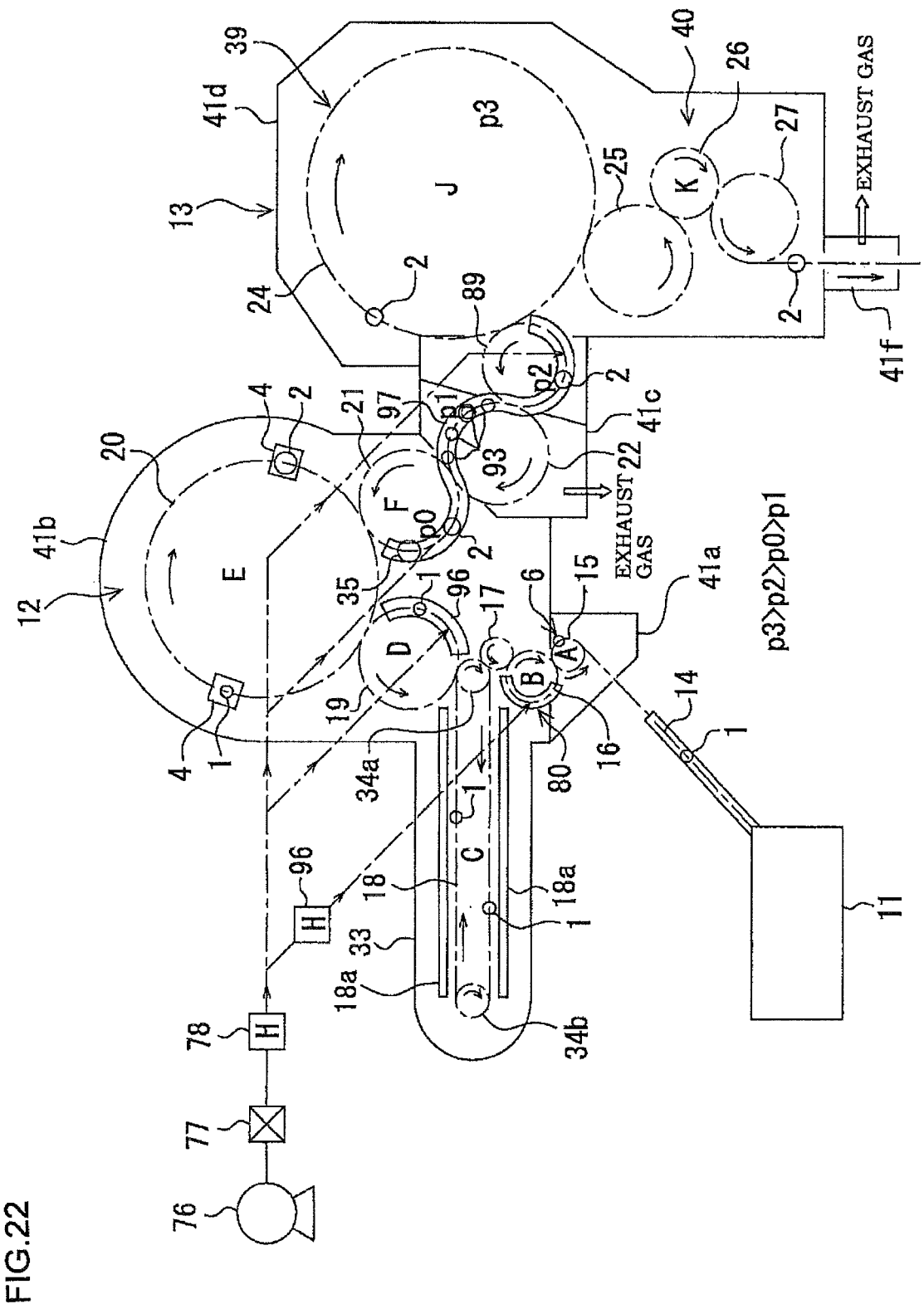
FIG. 22 is a plan view showing a further example of an aseptic filling system incorporating the bottle sterilizing apparatus.

Although the aseptic filling system of this seventh embodiment is constructed likely as shown in FIG. 22, the hydrogen peroxide supplying method is different from that of the sixth embodiment with respect to the central portion in the cover 97.

That is, a plurality of generators, each as like as the sterilizer gas generator 7 shown in FIG. 4, are disposed to portions corresponding to the central portion of the cover 97. By supplying the hydrogen peroxide gas G generated by such sterilizer gas generators 7 to the central portion in the cover 97, the hydrogen peroxide mist M is atomized directly upward so that the hydrogen peroxide adheres to the inner and outer surfaces of the battle 2 now traveling in the cover 97. In FIG. 22, reference numeral 93 is a hydrogen peroxide supplying nozzle of the sterilizer gas generator 7.

In this seventh embodiment, the like reference numerals are added to components and members corresponding to those of the other embodiments, and the detailed descriptions thereof will be omitted herein.

EXAMPLES

The amount of hydrogen peroxide adsorbed by the preform and the sterilization effect of the hydrogen peroxide on the inner surface of the preform were examined. Table 2 shows the result.

Experimental Example No. 1

Hydrogen peroxide gas of a concentration of 35% by mass was blasted into the preform at a flow rate of 6 g/min. The amount of hydrogen peroxide adhering to the inner surface of the preform was 0.028 $\mu L/cm^2$.

Experimental Example No. 2

The same amount of hydrogen peroxide as in the experimental example No. 1 was blasted into the preform. After that, hot air was blasted into the preform for 1.2 seconds. The blasted hot air vaporized the hydrogen peroxide in the preform and dried the interior of the preform, but part of the hydrogen peroxide was adsorbed by the preform (PET layer). The amount of the hydrogen peroxide adsorbed was 0.013 $\mu L/cm^2$. The amount of the hydrogen peroxide adsorbed was obtained by filling the preform with water, leaving the preform to stand for 24 hours and then measuring the amount of the hydrogen peroxide dissolved in the water.

Experimental Example No. 3

Hydrogen gas and hot air were blasted into the preform in the same manner as in the experimental example No. 2. Following the blasting of hot air, the preform was heated to 120° C. for 20 seconds. The sterilization effect on *B. atrophaeus* spore under this condition was checked, and the result was 6.0 LRV or higher. In addition, as in the experimental example No. 2, the amount of the hydrogen peroxide dissolved in water filling the preform was measured, and the amount of the remaining hydrogen peroxide was 0.006 $\mu L/cm^2$.

As is obvious from comparison between the experimental examples No. 2 and No. 3, if 0.007 (=0.013−0.006) $\mu L/cm^2$ of hydrogen peroxide adsorbed by the preform is heated and

TABLE 2

| No. | AMOUNT OF 35%-$H_2O_2$ SUPPLIED (g/min) | HOT AIR DURATION (sec) | PF HEATING (PERFORMED: PF TEMPERATURE AFTER 20 SECONDS OF HEATING IS 120° C.) | $\mu L/cm^2$ (AMOUNT OF 35%-$H_2O_2$ ADHERING TO OR ADSORBED BY INNER SURFACE OF PF) | REMARKS | STERILIZATION EFFECT (*B. atrophaeus*) |
|---|---|---|---|---|---|---|
| 1 | 6 | 0.00 | NOT PERFORMED | 0.028 | AMOUNT OF $H_2O_2$ ADHERING TO PF | |
| 2 | 6 | 1.2 | NOT PERFORMED | 0.013 | AMOUNT OF $H_2O_2$ ADSORBED BY PF | |
| 3 | 6 | 1.2 | PERFORMED | 0.006 | AMOUNT OF $H_2O_2$ REMAINING IN PF | >6.0 |
| 4 | 6 | 5.0 | NOT PERFORMED | 0.003 | AMOUNT OF $H_2O_2$ ADSORBED BY PF | |
| 5 | 6 | 5.0 | PERFORMED | 0.001 | AMOUNT OF $H_2O_2$ REMAINING IN PF | >6.0 |
| 6 | 6 | 10.0 | NOT PERFORMED | 0.001 | AMOUNT OF $H_2O_2$ ADSORBED BY PF | |
| 7 | 6 | 10.0 | PERFORMED | 0.000 | AMOUNT OF $H_2O_2$ REMAINING IN PF | >6.0 | activated, a sterilization effect of 6.0 LRV or higher can be achieved on the inner surface of the preform.

Experimental Example No. 4

The preform was sterilized in a procedure similar to that in the experimental example No. 2. Unlike the experimental example No. 2, hot air was supplied for 5.0 seconds. The amount of the hydrogen peroxide adsorbed by the preform was 0.003 µL/cm$^2$.

Experimental Example No. 5

The preform was sterilized in a procedure similar to that in the experimental example No. 3. Unlike the experimental example No. 3, hot air was supplied for 5.0 seconds. The amount of the hydrogen peroxide remaining in the preform was 0.001 µL/cm$^2$. The sterilization effect was 6.0 LRV or higher.

As is obvious from comparison between the experimental examples No. 4 and No. 5, if 0.002 (=0.003−0.001) µL/cm$^2$ of hydrogen peroxide adsorbed by the preform is heated and activated, a sterilization effect of 6.0 LRV or higher can be achieved on the inner surface of the preform.

Furthermore, as is obvious from comparison between the experimental examples No. 3 and No. 5, if the duration of hot air supply is changed from 1.2 seconds to 5.0 seconds, the amount of the remaining hydrogen peroxide decreases from 0.006 µL/cm$^2$ to 0.001 µL/cm$^2$.

Experimental Example No. 6

The preform was sterilized in a procedure similar to that in the experimental example No. 4. Unlike the experimental example No. 4, hot air was supplied for 10.0 seconds. The amount of the hydrogen peroxide adsorbed by the preform was 0.001 µL/cm$^2$.

Experimental Example No. 7

The preform was sterilized in a procedure similar to that in the experimental example No. 5. Unlike the experimental example No. 5, hot air was supplied for 10.0 seconds. The amount of the hydrogen peroxide remaining in the preform was 0.000 µL/cm$^2$. The sterilization effect was 6.0 LRV or higher.

As is obvious from comparison between the experimental examples No. 6 and No. 7, if 0.001 (=0.001−0.000) µL/cm$^2$ of hydrogen peroxide adsorbed by the preform is heated and activated, a sterilization effect of 6.0 LRV or higher can be achieved on the inner surface of the preform.

Furthermore, as is obvious from comparison between the experimental examples No. 6 and No. 7, if the duration of hot air supply is changed from 5.0 seconds to 10.0 seconds, the amount of the remaining hydrogen peroxide decreases from 0.001 µL/cm$^2$ to an undetectable amount.

For example, as described in Japanese Patent No. 4012653, according to conventional art, the amount of adsorbed hydrogen peroxide required to sterilize the bottle is 5 µL to 100 µL. Since the inner surface area of the preform for a 500 ml bottle is approximately 500 cm$^2$, the amount of adsorbed hydrogen peroxide of 0.001 to 0.006 µL/cm$^2$ in the examples of the present invention described above translates to 0.5 µL to 3 µL. In short, according to the present invention, only an extremely small amount of hydrogen peroxide that is 1/33 to 1/10 of the amount of hydrogen peroxide required according to conventional art is required to sterilize a bottle, and a sterilization effect of 6 LRV or higher on spore-forming bacteria is achieved with the extremely small amount of adsorbed hydrogen peroxide of 0.001 to 0.006 µL/cm$^2$. This sterilization effect is a level that enables aseptic filling.

In the experimental examples No. 3, No. 5 and No. 7, the preform was heated in the heating furnace of the blow-molding machine. In the blow-molding machine, however, corrosion or the like of various devices such as a packing in the blow-molding machine was not observed.

REFERENCE NUMERAL

1 - - - preform, 2 - - - bottle, 4 - - - mold, 6 - - - nozzle, 9 - - - evaporator, 80 - - - air nozzle, 80a - - - blasting port, G - - - gas, P - - - hot air.

The invention claimed is:

1. A method of sterilizing a bottle, comprising the steps of:
gasifying a hydrogen peroxide solution to a hydrogen peroxide solution gas and discharging the hydrogen peroxide solution gas from a discharge port of a nozzle, which has a discharging direction, the nozzle having a lower end that has an inner annular lower edge surface and an outer annular lower edge surface, which extend along a common plane in a direction perpendicular to the discharging direction, with an annular groove having an approximately semi-circular downwardly curved shaped surface interposed therebetween, such that each surround the discharge port of the nozzle, whereby the lower end of the nozzle is positioned above a preform, which has an opening in a mouth portion of the preform, such that the inner annular lower edge surface and the outer annular lower edge surface, which have the annular groove interposed therebetween, are positioned above the opening in the mouth portion of the preform, thereby discharging and guiding the hydrogen peroxide solution gas toward inner and outer surfaces of the preform made of resin;
letting the preform adsorb 0.001 µL/cm$^2$~0.013 µL/cm$^2$ of a condensed film of the hydrogen peroxide solution, with the film of the hydrogen peroxide solution containing a concentration of 35% by mass of hydrogen peroxide, adhering to the surfaces of the preform while an excess of the film of the hydrogen peroxide solution remains on the surfaces of the preform;
blasting an air to the preform before conveying the preform into a heating furnace, only from a blasting nozzle that is at a predetermined distance away from the preform having the film of the hydrogen peroxide solution adhering thereto to remove the excess of the film of the hydrogen peroxide solution from both the inner and outer surfaces of the preform as the preform is adsorbing the hydrogen peroxide solution;
conveying the preform into the heating furnace and sterilizing the preform by heating the preform having adsorbed the hydrogen peroxide solution to a temperature suitable for a blow-molding treatment to activate the hydrogen peroxide solution adsorbed by the preform; and
shaping the preform into the bottle by blowing air into the preform in a mold,
wherein the above-mentioned steps are performed sequentially.

2. The bottle sterilizing method according to claim 1, wherein the preform is allowed to adsorb the hydrogen peroxide solution by atomizing the hydrogen peroxide solution in an evaporator to gasify the hydrogen peroxide solution and discharging the hydrogen peroxide solution gas toward the surfaces of the preform from the discharge port of the nozzle.

3. The bottle sterilizing method according to claim 1, wherein, in the step of gasifying the hydrogen peroxide solution to the hydrogen peroxide solution gas, the hydrogen peroxide solution includes at least 1% by mass of a hydrogen peroxide component.

4. The bottle sterilizing method according to claim 1, wherein an umbrella-shaped member covers above the mouth portion of the preform at a time when the preform is heated to the temperature for the blow-molding step.

5. The bottle sterilizing method according to claim 1, wherein an aseptic air is blasted to the mouth portion of the preform at a time when the preform is conveyed toward the mold after heating the preform to the temperature for the blow-molding step.

6. The bottle sterilizing method according to claim 2, wherein, when atomizing the hydrogen peroxide solution in the evaporator to gasify the hydrogen peroxide solution, the hydrogen peroxide solution includes at least 1% by mass of a hydrogen peroxide component.

\* \* \* \* \*